(12) United States Patent
Filipe et al.

(10) Patent No.: US 11,067,569 B2
(45) Date of Patent: Jul. 20, 2021

(54) METHOD OF STABILIZING MOLECULES WITHOUT REFRIGERATION USING WATER SOLUBLE POLYMERS AND APPLICATIONS THEREOF IN PERFORMING CHEMICAL REACTIONS

(71) Applicant: McMaster University, Hamilton (CA)

(72) Inventors: Carlos Filipe, Ancaster (CA); John D. Brennan, Dundas (CA); Robert Pelton, Dundas (CA); Sana Jahanshahi-Anbuhi, Hamilton (CA); Yingfu Li, Dundas (CA)

(73) Assignee: MCMASTER UNIVERSITY, Hamilton (CA)

( * ) Notice: Subject to any disclaimer, the term of this patent is extended or adjusted under 35 U.S.C. 154(b) by 0 days.

(21) Appl. No.: 16/274,616

(22) Filed: Feb. 13, 2019

(65) Prior Publication Data

US 2019/0178880 A1 Jun. 13, 2019

Related U.S. Application Data

(63) Continuation of application No. 15/034,914, filed as application No. PCT/CA2014/051081 on Nov. 10, 2014, now Pat. No. 10,241,109.

(60) Provisional application No. 61/901,784, filed on Nov. 8, 2013.

(51) Int. Cl.
| | |
|---|---|
| G01N 33/543 | (2006.01) |
| G01N 21/78 | (2006.01) |
| G01N 33/548 | (2006.01) |
| C12Q 1/66 | (2006.01) |
| C12Q 1/686 | (2018.01) |
| G01N 21/77 | (2006.01) |

(52) U.S. Cl.
CPC ........... *G01N 33/5436* (2013.01); *C12Q 1/66* (2013.01); *C12Q 1/686* (2013.01); *G01N 21/78* (2013.01); *G01N 33/548* (2013.01); *G01N 2021/7786* (2013.01); *G01N 2333/922* (2013.01)

(58) Field of Classification Search
CPC .. G01N 33/5436; G01N 33/548; G01N 21/78; G01N 2021/7786; C12Q 1/66; C12Q 1/686
USPC ....................................................... 536/124
See application file for complete search history.

(56) References Cited

U.S. PATENT DOCUMENTS

| | | | |
|---|---|---|---|
| 6,449,925 B1 | 9/2002 | Kyoichi et al. | |
| 6,596,298 B2 | 7/2003 | Leung et al. | |
| 7,022,514 B2 | 4/2006 | Vodyanoy et al. | |
| 7,101,693 B2 | 9/2006 | Cicerone et al. | |
| 7,604,807 B2 | 10/2009 | Vodyanoy et al. | |
| 7,749,538 B2 | 7/2010 | Sugimoto et al. | |
| 7,972,618 B2 | 7/2011 | Fuisz et al. | |
| 8,105,625 B2 | 1/2012 | Rajewski et al. | |
| 10,241,109 B2 * | 3/2019 | Filipe | G01N 21/78 |
| 2002/0049181 A1 | 4/2002 | Cornelis et al. | |
| 2005/0070701 A1 | 3/2005 | Hochstetler et al. | |
| 2009/0162516 A1 | 6/2009 | Brown et al. | |
| 2009/0253754 A1 | 10/2009 | Selmin et al. | |
| 2010/0068350 A1 | 3/2010 | Shen et al. | |
| 2011/0305768 A1 | 12/2011 | Jiang et al. | |
| 2018/0092851 A1 | 4/2018 | Hassett et al. | |
| 2018/0326039 A1 | 11/2018 | Haruta | |
| 2019/0275136 A1 | 9/2019 | Kosuda et al. | |

FOREIGN PATENT DOCUMENTS

| | | |
|---|---|---|
| JP | 2000159788 A | 6/2000 |
| WO | 2008124617 A2 | 10/2008 |
| WO | 2019195350 A1 | 4/2019 |

OTHER PUBLICATIONS

International Search Report and Written Opinion of corresponding international application No. PCT/CA2014/051081 dated Jan. 21, 2015.
Jahanshahi-Anbuhi, Sana et al., "Pullulan Encapsulation of Labile Bimolecules to Give Stable Bioassay Tablets", Agnew. Chem. Inter. Ed., Jun. 10, 2014, 53(24), pp. 6155-6158 and Supporting Information.
Intellectual Ventures/Global Good Presentation, "Simple Method for Stabilizing Labile Agents", Apr. 18, 2014.
Presentation, "Firefly Luciferase-Pullulan Pill for Detection of ATP", Jun. 2014.
S. Jahanshahi-Anbuhi et al. Chem. Sci., 2016, 7, S1-S8.
Leung, V., et al., "Thermal Stabilization of Viral Vaccines in Low-Cost Sugar Films", Scientific Reports, 9(1), 1-11, May 21, 2019.

(Continued)

*Primary Examiner* — Yih-Horng Shiao
(74) *Attorney, Agent, or Firm* — Bereskin & Parr LLP/S.E.N.C.R.L., S.R.L.; Patricia Folkins

(57) ABSTRACT

The present application is directed to methods of performing chemical reactions, including multi-step chemical reactions in which two or more of the reagents in the chemical reaction are incorporated or entrapped in a solid polymeric structure comprising pullulan. In certain embodiments, the chemical reaction or multi-step reaction serves as a sensor. Accordingly the present application is also directed to sensors for performing the methods of the application. In certain embodiments, at least one of the reagents is a biomolecule and the sensor is a biosensor. In certain other embodiments, the solid polymeric structure comprising pullulan and the reagents for performing a chemical reaction form a convenient device for performing a chemical reaction.

19 Claims, 35 Drawing Sheets

Specification includes a Sequence Listing.

(56) References Cited

OTHER PUBLICATIONS

Teekamp, Naomi, et al., "Addition of Pullulan to Trehalose Glasses Improves the Stability of B-Galactosidase at High Moisture Conditions", Carbohydrate Polymers 176 pp. 374-380, 2017.
Pelliccia, Maria et al., "Additives for vaccine storage to improve thermal stability of adenoviruses from hours to months", Nature Communications 7:13520, 2016.
Bajrovic, Irnela et al. "Novel technology for storage and live vaccines and other biological medicines at ambient temperature", Science Advances, vol. 6, 1-13, Mar. 2020.
Cicerone, Marcus T., et al. "Fast Dynamics and Stabilization of Proteins: Binary Glasses of Trehalose and Glycerol", Biophysical Journal, vol. 86, pp. 3836-3845, Jun. 2004.
Mistilis, Matthew J., et al., "Long-term stability of influenza vaccine in a dissolving microneedle patch", Drug Delivery Trans! Res.7(2): 195-205; Apr. 2017.

\* cited by examiner

(A) Disc-Shaped Film

(B) Other Desired Pattern

*I. Hydrophobic Spray*

*II. Remove the Tapes*

*III. Add the Pullulan Solution*

*IV. Leave the Samples to Air Dry*

(A) Chemical Reactions

Enamine          Simon-Awe complex (i)      (ii)      (iii)

(B) Lateral Flow Format (X,Y Direction)

(C) Spot-Test Format (Z Direction)

SEQUENCE LISTING

```
<160> NUMBER OF SEQ ID NOS: 3

<210> SEQ ID NO 1
<211> LENGTH: 21
<212> TYPE: DNA
<213> ORGANISM: Artificial Sequence
<220> FEATURE:
<223> OTHER INFORMATION: Synthetic construct

<400> SEQUENCE: 1
caggtccatc gagtggtagg a                                                   21

<210> SEQ ID NO 2
<211> LENGTH: 21
<212> TYPE: DNA
<213> ORGANISM: Artificial Sequence
<220> FEATURE:
<223> OTHER INFORMATION: Synthetic construct

<400> SEQUENCE: 2
gtacgttcag gagcagtgcg a                                                   21

<210> SEQ ID NO 3
<211> LENGTH: 82
<212> TYPE: DNA
<213> ORGANISM: Artificial Sequence
<220> FEATURE:
<223> OTHER INFORMATION: Synthetic construct

<400> SEQUENCE: 3
caggtccatc gagtggtagg aggaggtatt tagtgccaag ccatctcaaa cgacgtctga        60
gtcgcactgc tcctgaacgt ac                                                  82
```

METHOD OF STABILIZING MOLECULES WITHOUT REFRIGERATION USING WATER SOLUBLE POLYMERS AND APPLICATIONS THEREOF IN PERFORMING CHEMICAL REACTIONS

This application is continuation of co-pending U.S. patent application Ser. No. 15/034,914, filed May 6, 2016, which is a national stage of International Application No. PCT/CA2014/051081 filed Nov. 10, 2014, which claims the benefit of U.S. provisional patent application No. 61/901,784, filed on Nov. 8, 2013, the contents of each of which are incorporated herein by reference in their entirety.

INCORPORATION OF SEQUENCE LISTING

A computer readable form of the Sequence Listing "3244-P46611US02_SequenceListing.txt" (4,096 bytes), submitted via EFS-WEB and created on Apr. 12, 2021, is herein incorporated by reference.

FIELD

The present application relates to methods for performing chemical reactions. In particular, the application is directed to methods in which two or more of the reagents for the chemical reaction are stabilized using water soluble polymers.

BACKGROUND

Almost all bioassays make use of bioreagents (such as enzymes and small-molecule substrates) that are labile to various degrees and require special shipping and storage. The instability of these molecules can arise from either thermal denaturation or chemical modification, such as oxidation or hydrolysis. Because of these issues, they often have to be shipped on dry ice with special packaging, which is costly. These reagents also have to be stored in bulk in refrigerators or freezers to minimize loss of activity, but they must be retrieved, thawed, and aliquoted for intended tests that are often performed at room temperature. Repeated freezing and thawing can result in significant loss of activity, which often leads to less reliable test results.

Pullulan is a natural polysaccharide produced by the fungus *Aureobasidium pullulans*.[1] It readily dissolves in water but resolidifies into films upon drying.[1a,1b,2] The film forming property of pullulan has been utilized in some unique applications in the pharmaceutical and food industries, such as breath fresheners and food additives.[1b,3] Recent studies have found that pullulan coatings applied to food packaging can act as oxygen barriers to prolong the shelf life of various foods.[2,4] In addition, pullulan has been shown to preserve the viability of bacteria under various storage conditions.[3]

U.S. Pat. No. 7,604,807 describes the reversible preservation of biological samples in compositions comprising natural polymers such as pullullan or acacia gum.

SUMMARY

It has been discovered that unstable biomolecules, such as enzymes, and other unstable organic molecules can be stabilized for long periods of time under ambient conditions when added to a pullulan solution and casted as, for example, a film or pill. Pullulan is a non-ionic carbohydrate, which is approved as a food additive and deemed safe. Addition of water or buffer to a pullulan-doped solid polymeric structure generates a solution with active molecules. This discovery may be used to circumvent the need of cold condition for storage and distribution for a variety of labile agents such as vaccines, and enzymes and reagents for performing chemical reactions. It was also found that because pullulan films are impermeable to oxygen, they can be used to preserve molecules that are easily oxidized.

In particular aspects of the present application the incorporation of unstable molecules into pullulan has been found to facilitate and simplify chemical reactions with these molecules. The molecules are conveniently packaged in pullulan polymeric structures and stored/packaged until the chemical reaction is needed or desired. This finding is advantageous, for example, for the development of sensors that comprises sensitive biomolecules.

By placing reagents for a chemical reaction, for example reagents to perform an assay, into a pullulan polymeric structure, both premeasured quantities of reagents and addition of preservatives that can prolong the shelf life of the reagents are provided. It has been found herein that pullulan meets the following three conditions that are desirable for this application: 1) it allows the encapsulation of molecules, including biomolecules, in a form suitable for shipping; 2) it provides outstanding protection for entrapped molecules against thermal denaturation and chemical modification during shipping and storage; and 3) it is readily soluble in aqueous solution, allows the release of the encapsulated molecules, and does not interfere with the reaction(s) itself.

Accordingly, the present application includes a method of performing a single step or multi-step chemical reaction comprising:
 a) combining two or more reagents for the reaction, either separately or together, with an aqueous pullulan solution to provide reagent pullulan solutions or a reagent pullulan solution, respectively;
 b) drying the reagent pullulan solutions or the reagent pullulan solution to provide solid polymeric structures or a solid polymeric structure, respectively; and
 c) if the two or more reagents are in separate solid polymeric structures in b), then treating the solid polymeric structures under conditions to dissolve the solid polymeric structures and for the reagents to interact in a chemical reaction; or
 d) if the two or more reagents are together in the solid polymeric structure in b), then treating the solid polymeric structure under conditions to dissolve the solid polymeric structure and for the reagents to interact in a chemical reaction.

The present application also includes sensors or devices comprising two or more reagents entrapped in the same solid polymeric structure or in different solid polymeric structures wherein the solid polymeric structure(s) are comprised of pullulan. In an embodiment, at least one of the two or more reagents is a biomolecule and the sensor is a biosensor.

In certain embodiments, the materials that are immobilized are inorganic or organic molecules, proteins, enzymes, antibodies, RNA, DNA, phage, viruses, anaerobic and aerobic bacteria, mammalian cells, vaccines or a combination thereof.

In other embodiments, the application includes a biosensor comprising one or more water soluble films containing an active ingredient whereby addition of water or a buffer brings the active components in contact with each other.

Other features and advantages of the present application will become apparent from the following detailed description. It should be understood, however, that the detailed description and the specific examples, while indicating embodiments of the application, are given by way of illustration only and the scope of the claims should not be limited by these embodiments, but should be given the broadest interpretation consistent with the description as a whole.

DRAWINGS

The embodiments of the application will now be described in greater detail with reference to the attached drawings in which:

FIG. 1A shows approach I for a chemical reaction, in an exemplary embodiment of the application, wherein at least two of the reagents are in separate solid polymeric structures (enzyme as a film, substrate as a pill) includes the preparation and testing methods: a) preparation of the enzyme film: enzyme/pullulan solution is casted in an Eppendorf tube, and left open to dry. b) preparation of substrate pill: substrate/pullulan solution is casted in mold with wells size of: 3 mm diameter×3 mm depth. c) pesticide detection test.

FIG. 1B shows approach II for a chemical reaction, in an exemplary embodiment of the application, wherein at least two of the reagents are in separate solid polymeric structures: (a) demonstration of the method of constructing a capsule. For the purposes of nested capsules, different sizes are used. The liquid medium that the AChE and IDA is dissolved in should not be able to dissolve pullulan (ethanol/methanol for the IDA, Tris for the AChE) (b) demonstrates a suggested method of operation for the capsule sensor. It is desirable to have either a small volume of sample for qualitative analysis, or a small, precisely known volume of sample for quantitative analysis, which is why it is suggested to utilize a standard container that will result in consistent sample volumes.

FIG. 2 shows (a) images of exemplary cast pullulan capsules. Capsules are formed from 200 μL of 100 mg/mL pullulan solution, therefore approximately 20 mg of pullulan is used per capsule. (b) Schematic diagram of each exemplary capsule's dimensions, as well as the mold that the capsules are cast into.

FIG. 3 shows images of the different sized capsules in exemplary embodiments of the application. All capsules are cast from 200 mg/mL pullulan solution, and are ~4 mm tall. The diameters are 2, 3, 4 mm respectively.

FIG. 4 shows schematic diagrams of proposed capsule molds in exemplary embodiments of the application. (a) demonstrates an angled entrance to the mold, which should assist in the removal of the capsule, as well as provide a large surface to assist in sealing the capsule with a film. (b) represents a proposed mold design in which the mold can be split into two parts, in order to allow for very easy removal of the capsule. Some clamping mechanism holds the two halves together when allowing the films to dry.

Figure 7:
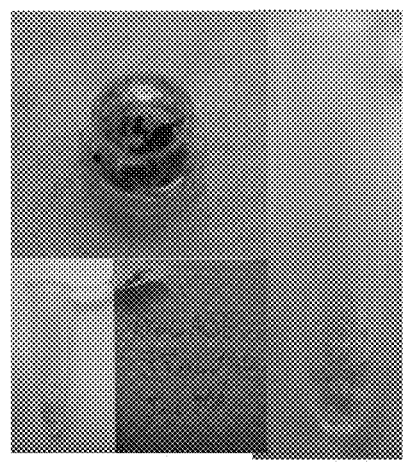

FIG. 7 shows (a) an exemplary pullulan capsule containing a red dye powder, used to determine if the capsule leaks, while (b) and (c) represents the color change that results when a single exemplary capsule containing 5 uL of IDA is added with 35 uL of water to the Eppendorf tube containing 50 uL of 250 mg/mL pullulan and 10 uL of AChE enzyme. While difficult to see due to the picture quality, there is a distinct blue color change indicating activity of both the enzyme and the substrate.

Figure 8:
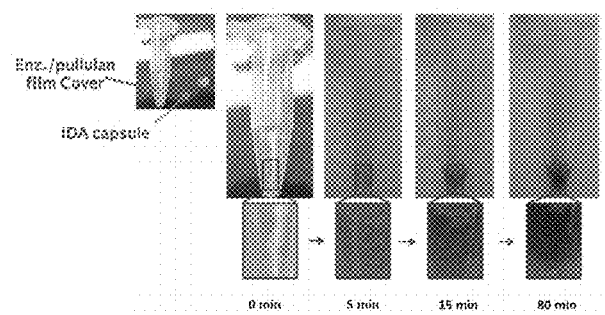

FIG. 8 shows images of color intensity of the reaction over time in an exemplary sensor of the application. As can be seen, the reaction begins to approach completion at time 15 minutes, and the color intensity change is lessened. To generate the color, 5 μL of AChE was added to 40 μL of 250 mg/mL pullulan solution, and cast into a 0.6 mL Eppendorf microcentrifuge tube. A 2 mm (diam)×4 mm (depth) capsule with an enlarged flange was filled with 5 μL of iDA (cap thickness of 5 mL, diam of 5/32"), and added to the Eppendorf tube 5 days after casting. 30 μL of dH$_2$O was added to the tube, to dissolve the capsule and allow for the reaction to occur.

Figure 9:
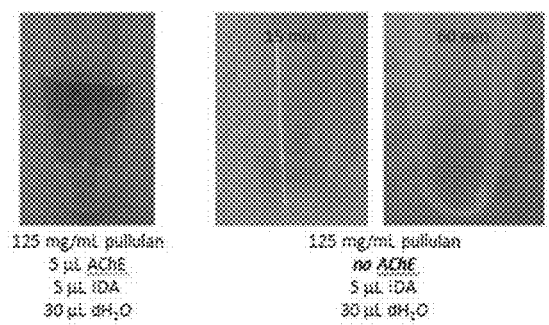

FIG. 9 shows images of a sample with dH$_2$O, and a control sample tested with no enzyme present in an exemplary sensor of the application. The control sample exhibited a slight color change after 60 minutes, but remained clear until 15 minutes, which is the typical sensing time.

Figure 10:
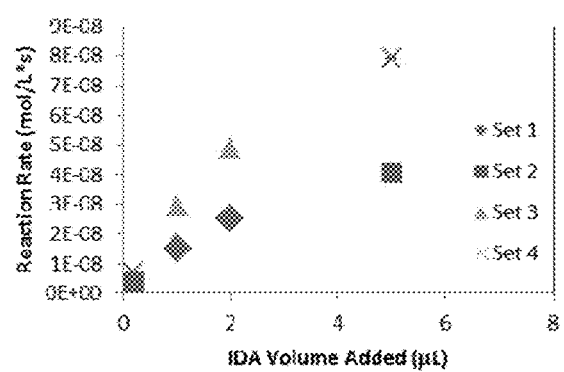

FIG. 10 is a plot of the reaction rate as a function of the volume of IDA added to the Eppendorf tube in an exemplary sensor of the application. It is expected that a higher reaction rate would result in a more intense color change in the allotted 15 minute time interval.

Figure 11:
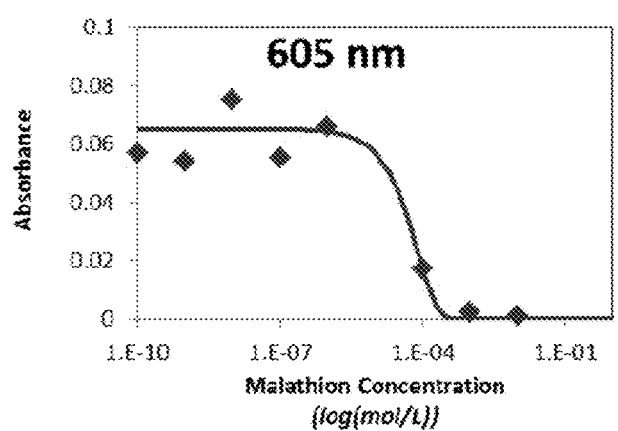

FIG. 11 shows plots of the absorbance measured for each sample solution as a function of the concentration of pesticide added to the sample in an exemplary sensor of the application. A wavelength of 605 was used to ensure that the correct trend is observed.

Figure 12:
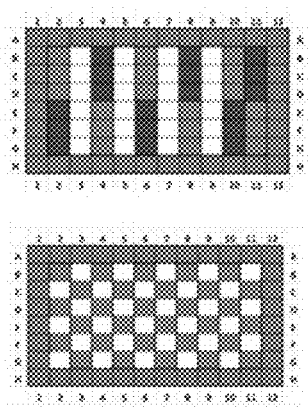

FIG. 12 shows images of the different well-patterns used in exemplary sensors of the application. When the pattern illustrated in (a) was used, it was determined that the center well usually resulted in a higher absorbance reading, most likely due to some sort of shadowing effect. Accordingly, the wells were spaced out as illustrated in (b), which allows for a total of 30 samples to be analysed each time.

Figure 13:
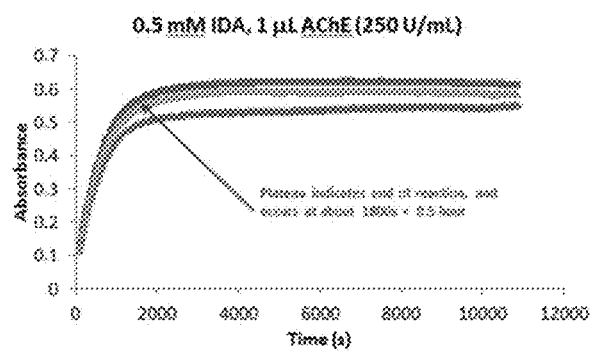

FIG. 13 is a plot of the absorbance as a function of time for a 0.5 mM IDA solution from an exemplary sensor of the application. The absorbance plateaus as the reaction nears completion, at about 30 minutes.

Figure 14:
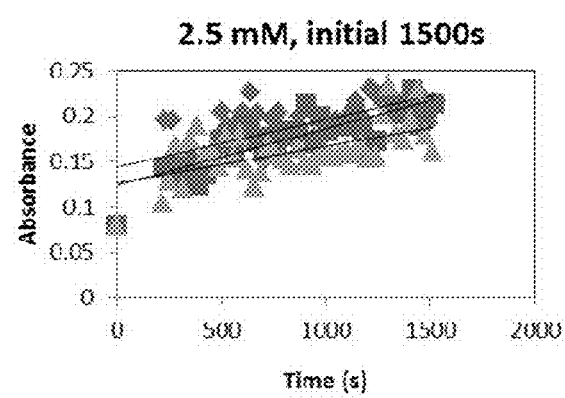

FIG. 14 is a plot of the absorbance as a function of time for the 2.5 mM case using an exemplary sensor of the application. The initial point of (0,00.03) is determined by a blank sample. The time delay before the start of measurements represents the setup time from when the IDA is added to when the plate is read in the Tecan. 1 uL of AChE (250 U/mL), 194 uL Tris buffer and 5 uL of IDA in MeOH brings the total well volume to 200 uL.

Figure 15:
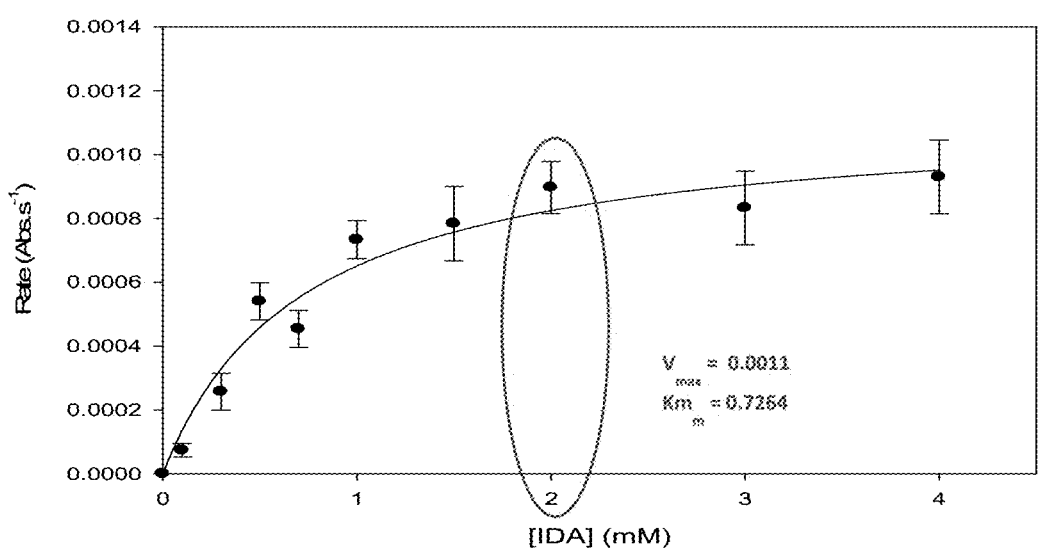

FIG. 15 shows plots of the reaction rate (abs*s−1) as a function of the IDA concentration from 0 to 4 mM using an exemplary sensor of the application. Plots are constructed with Sigma software, with the error bars representing three standard deviations based on triplicate repeats. The kM and the vmax values agree between plots. (a) represents the 0-500 s case, while (b) represents the 0-1500 s case.

Figure 16:
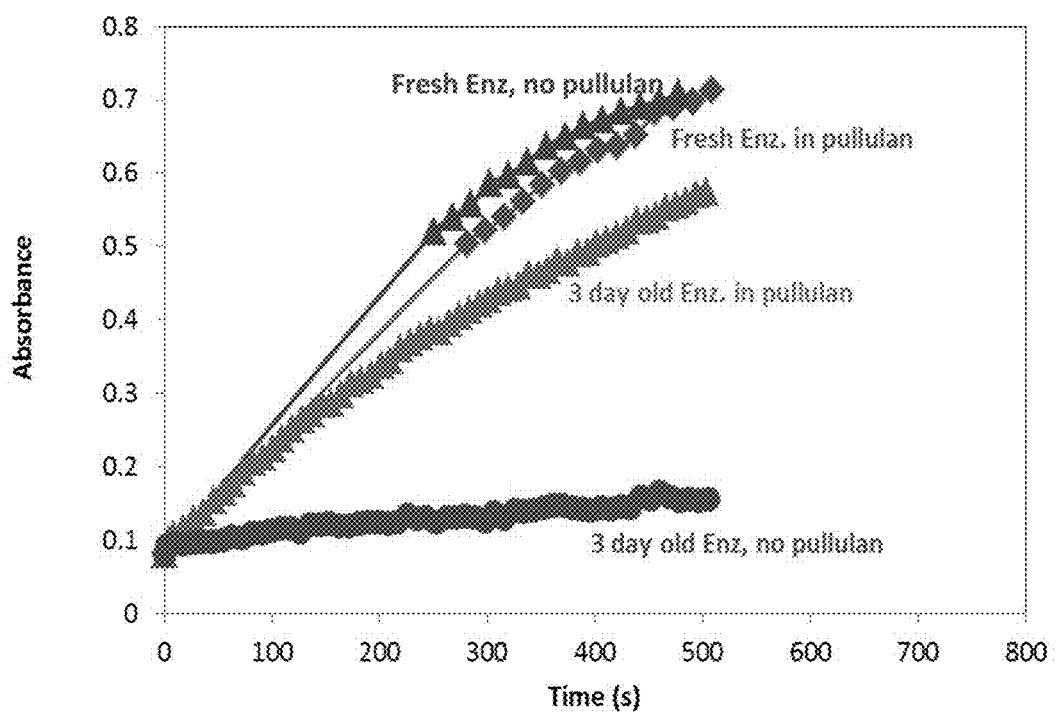

FIG. 16 is a plot of absorbance vs. time for the three trials using an exemplary sensor of the application. It is evident that the reaction rate observed was faster for the fresh pullulan than the 10 day old pullulan. Additionally, the initial slope of the solution with no pullulan was higher than that with pullulan. However, the final value of the solution without pullulan is both lower than the absorbance of the solutions with pullulan.

Figure 17:
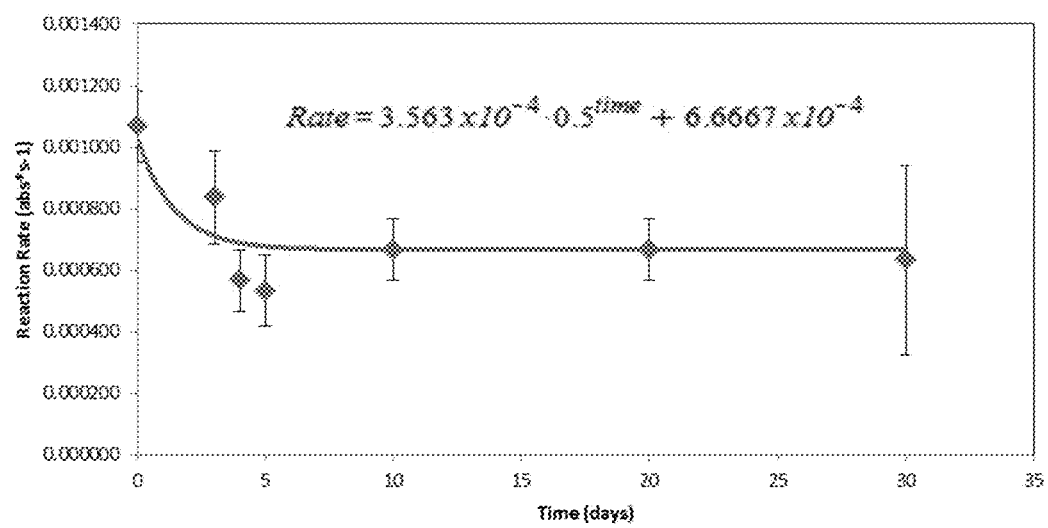
Figure 17:
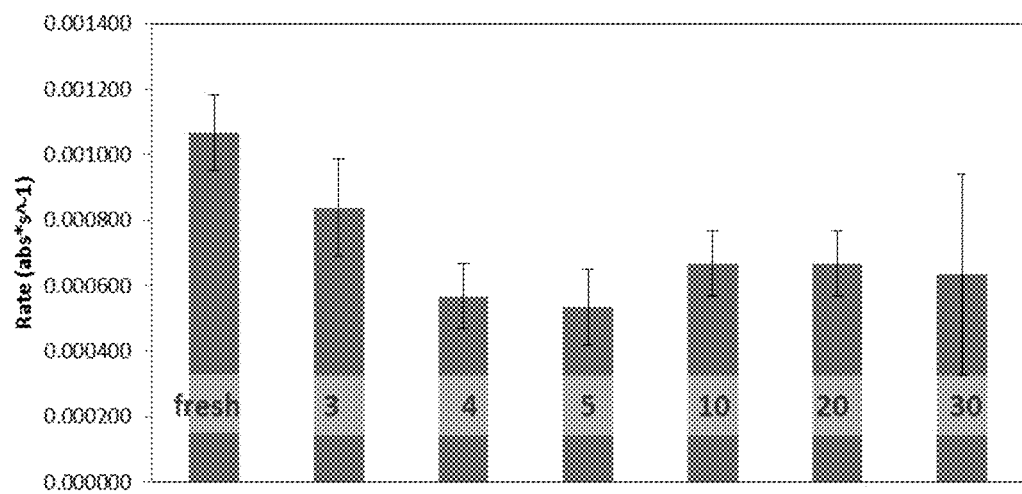

FIG. 17 is a plot of the corrected reaction rate (abs*s−1) over time using an exemplary sensor of the application. The activity decreased to a mean of approximately 63% activity as compared to a fresh sample. This is an acceptable decrease in activity over 30 days, especially when it is considered that when AChE without any pullulan is left out for 24 hours, it is completely inactivated (the rate of reaction is equal to the rate of auto-hydrolyzation of IDA, indicating complete inactivation of the enzyme).

Figure 18:
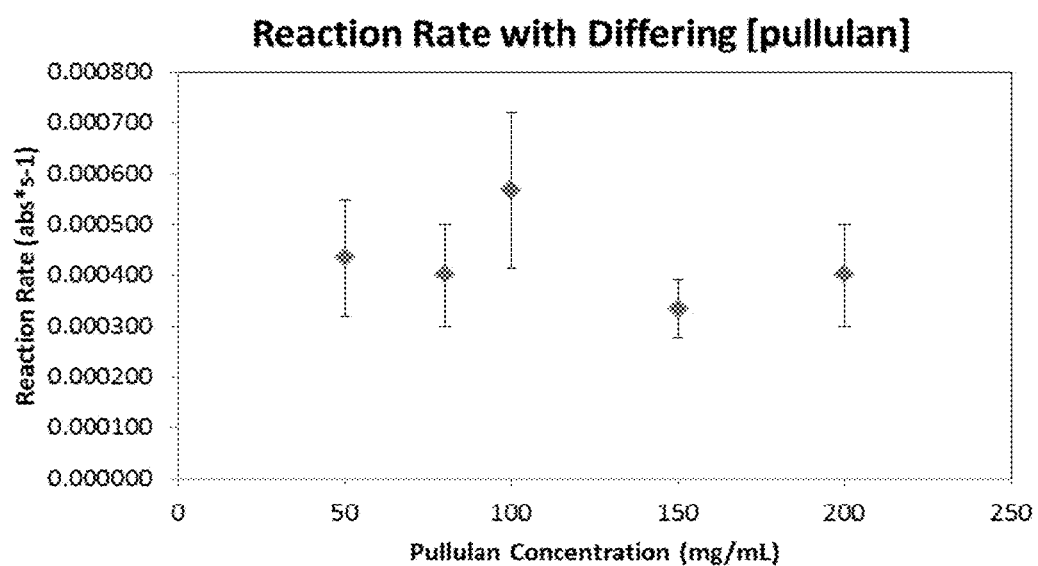

FIG. 18 shows a plot of the reaction rate of the enzyme (AChE) as a function of the pullulan concentration using an exemplary sensor of the application.

Figure 19:
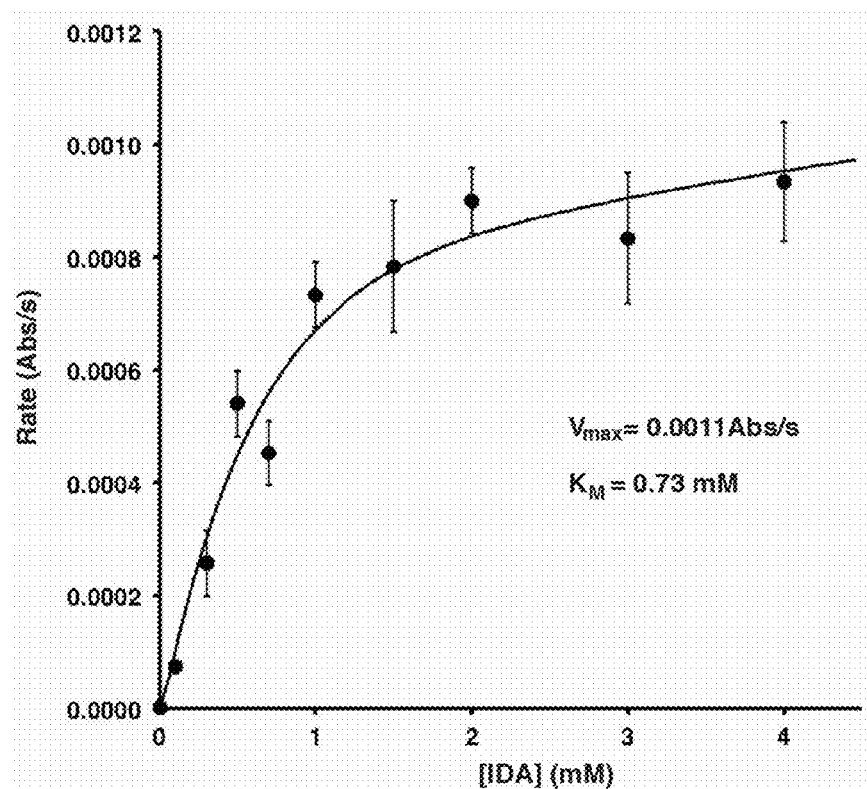

FIG. 19 shows a graph of the reaction rate (abs/s) of AChE and IDA as a function of the IDA concentration from 0 to 4 mM using an exemplary sensor of the application. The reaction rate of AChE tablet with different concentrations of IDA was monitored to establish an optimal IDA concentration for pesticide detection experiment. From the data, the concentration of IDA for the pesticide was chosen to be 2 mM (which is significantly larger than KM). The error bars represent the standard deviations based on triplicate repeats.

Figure 20:
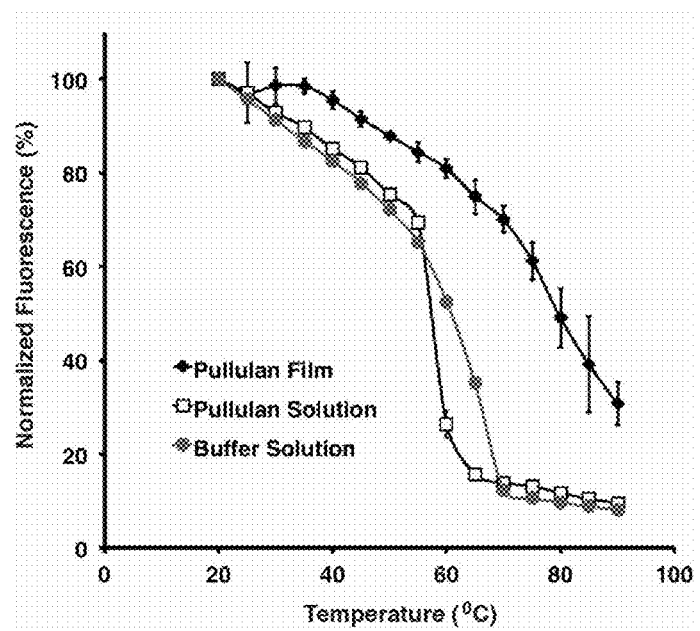

FIG. 20 shows fluorescence intensity-based thermal unfolding curves for HSA-buffer solution, in HSA-pullulan solution and HSA-pullulan film. Changes in the intrinsic fluorescence from tryptophan (Trp) residues within proteins can be used to provide information on protein conformational stability and unfolding.[5] Therefore, steady-state fluorescence spectra were measured at various temperatures for HSA-buffer solution, HSA-pullulan solution and HSA-pullulan film (HSA was chosen for this study because it contains a single Trp allowing for unambiguous investigation). The data shows that the intensity of fluorescence for HSA-buffer and HSA-pullulan solution decreased by more than 90% when the temperature was raised from 20° C. to 90° C., while that of HSA-pullulan film only decreased by ~70%. The unfolding temperature (wherein the Trp intensity is reduced by 50%) was significantly higher for the pullulan-HSA film at ~80° C., versus ~60° C. for both HSA-buffer and HSA-pullulan solutions. While not wishing to be limited by theory, this study demonstrates that pullulan film significantly enhances the thermal stability by preventing substantial unfolding as a result of molecular confinement in the rigid matrix. This stabilizing effect is only observed in the pullulan film and not in the pullulan solution.

Figure 21:
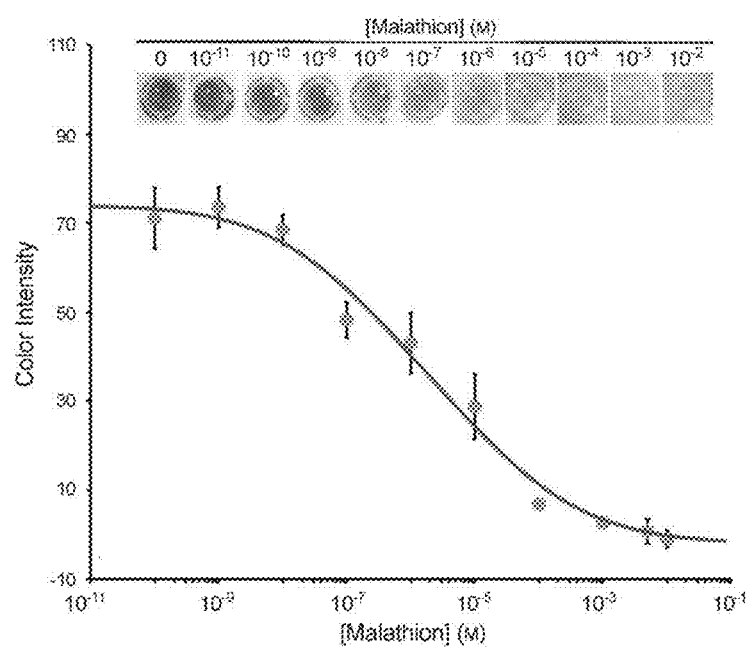

FIG. 21 is a graph showing dose-dependent inhibition of AChE at varying concentrations of malathion using an exemplary sensor of the application.

Figure 22:
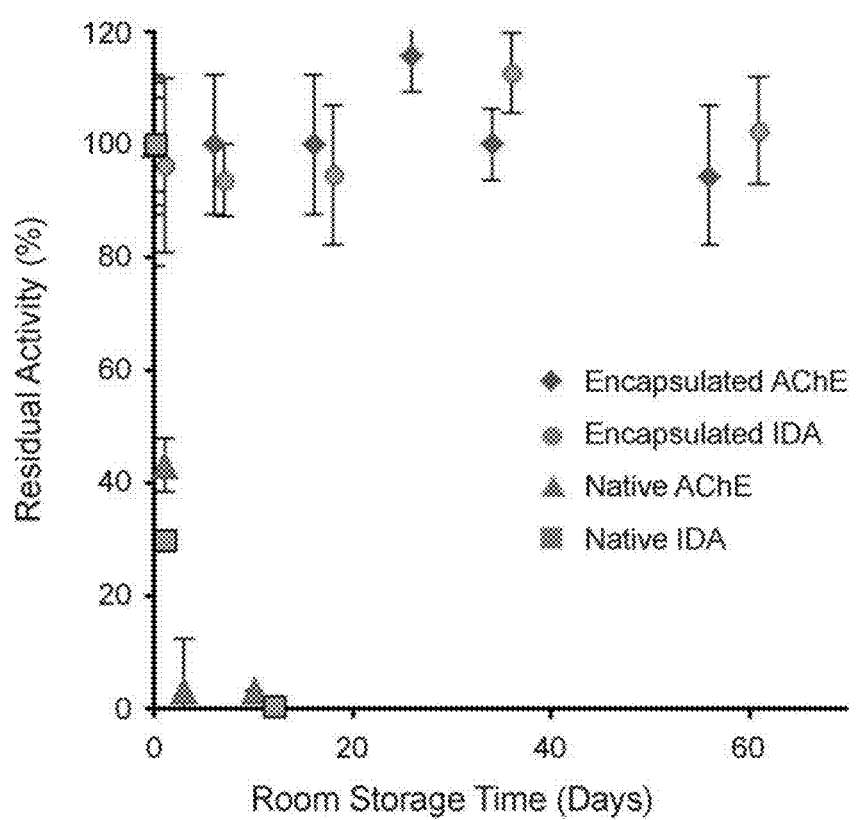

FIG. 22 shows the evaluation of the long-term stability of AChE and IDA tablets stored at room temperature in exemplary embodiments of the application. Normalized activity of encapsulated AChE in reaction with fresh IDA, encapsulated IDA in reaction with fresh AChE, unencapsulated (native) AChE in reaction with fresh substrate, and unencapsulated IDA in reaction with fresh AChE.

Figure 23:
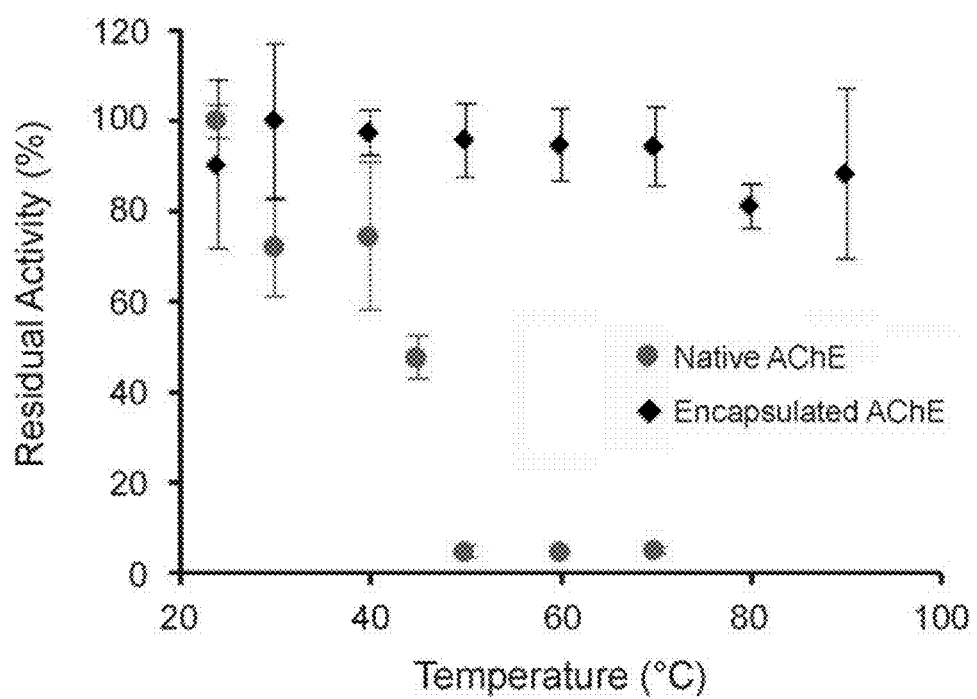

FIG. 23 shows loss of AChE activity as a function of temperature in exemplary embodiments of the application. Both encapsulated AChE and native enzyme were assessed.

Figure 24:
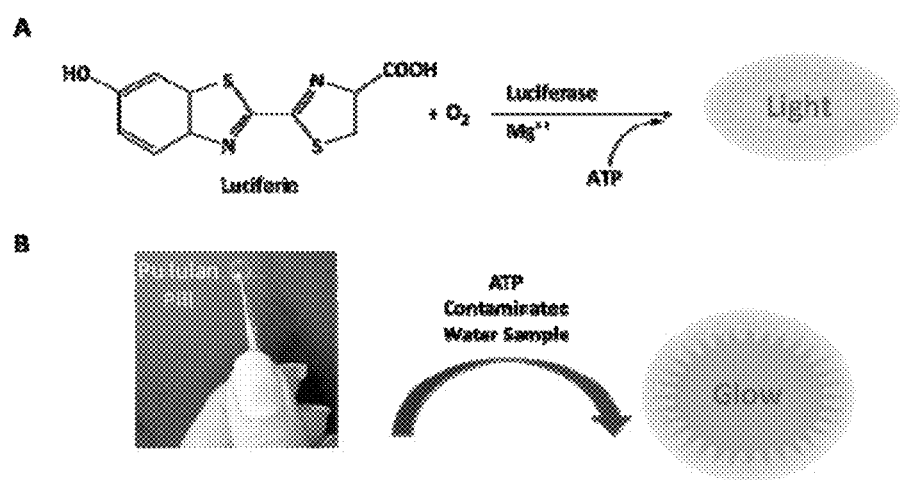

FIG. 24 is a schematic showing the pill assay for ATP as an exemplary sensor of the application. (a) Firefly luciferase reaction. (b) Operation principle of the assay using 'all-in-one' pill.

Figure 25:
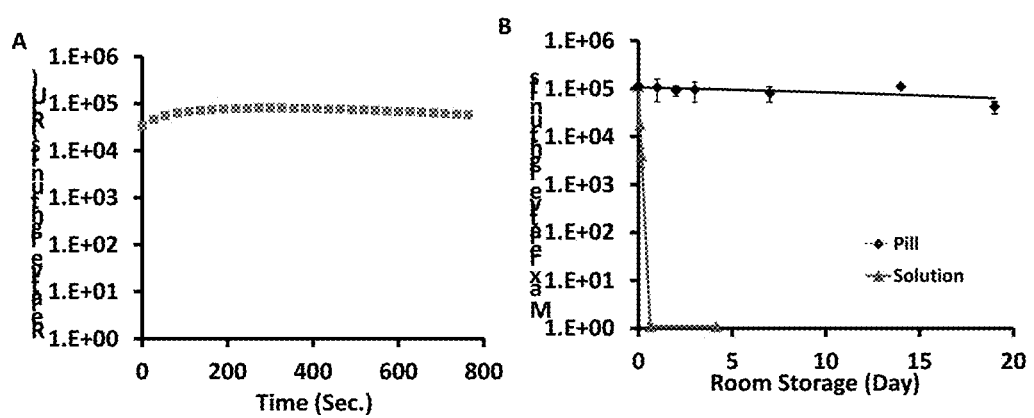

FIG. 25 shows A) Glow kinetics of the exemplary 'all-in-one' pill after one week of preparation and stored at room temperature; B) Stability of the pills over three weeks. The error bar represents triplicate measurements at each time interval.

Figure 26:
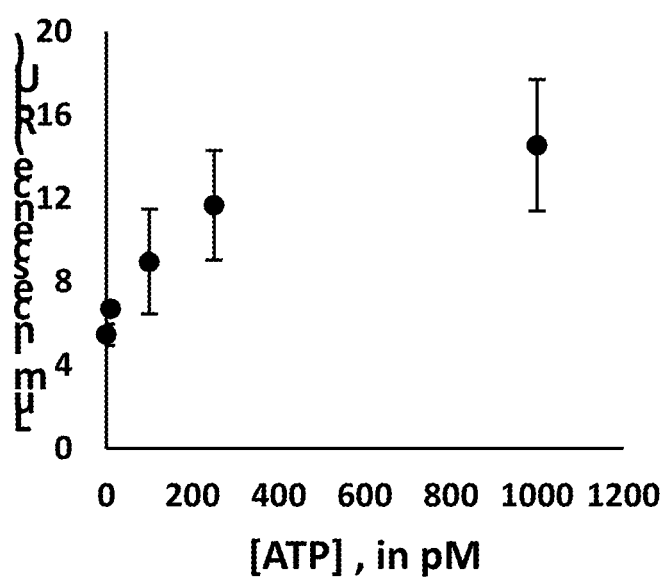

FIG. 26 shows detection of ATP is solution using the exemplary 'all-in-one' pills via a plot of the light intensity versus ATP concentration ranging from 10 pM to 1000 pM in tricine buffer. The error bars represent triplicate measurements at each concentration.

Figure 27:
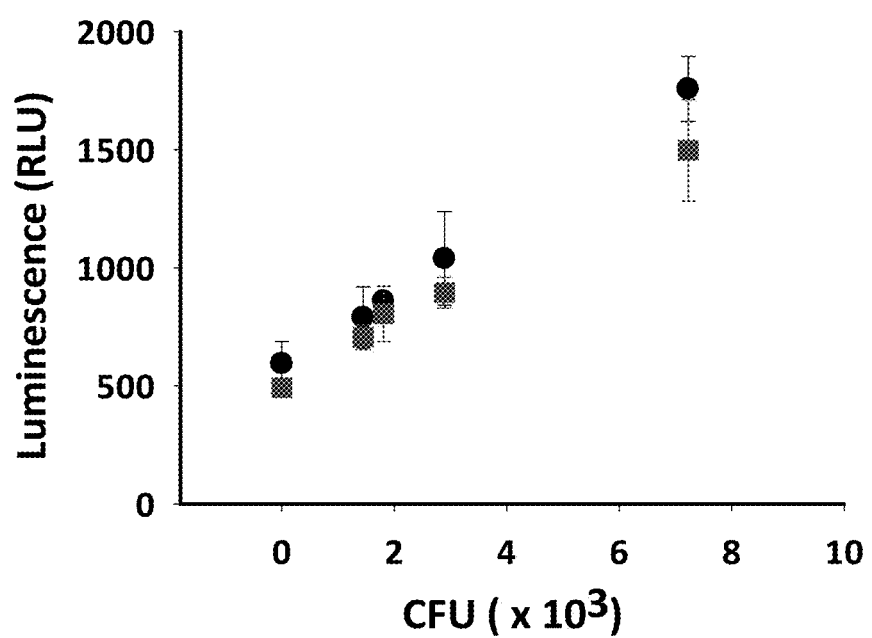

FIG. 27 shows detection of lysed (darker circles) and intact (lighter circles) E.Coli cells using the 'all-in-one' luminescent pill as an exemplary sensor of the application.

Figure 28:
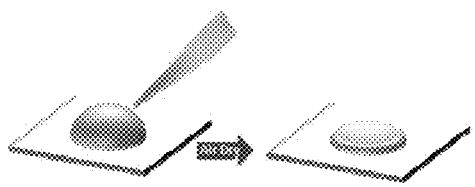
Figure 28:
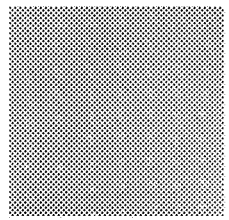
Figure 28:
Figure 28:
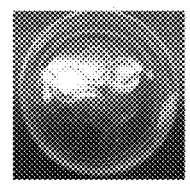
Figure 28:
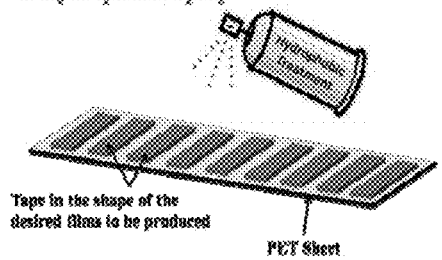
Figure 28:
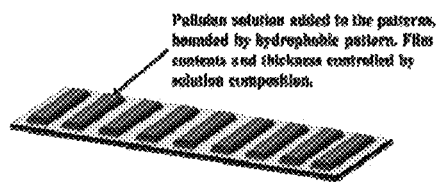
Figure 28:
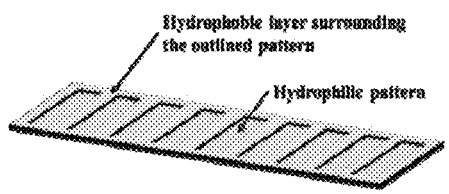
Figure 28:
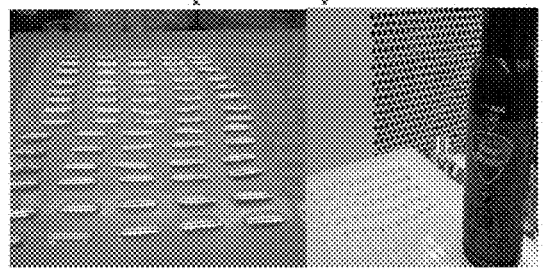

FIG. 28 shows the creation of exemplary pullulan films in (A) disc-shapes which are created by pipetting the pullulan mixture on surface of the flexible transparency PET sheet, and (B) other desired shapes and dimension.

Figure 29:
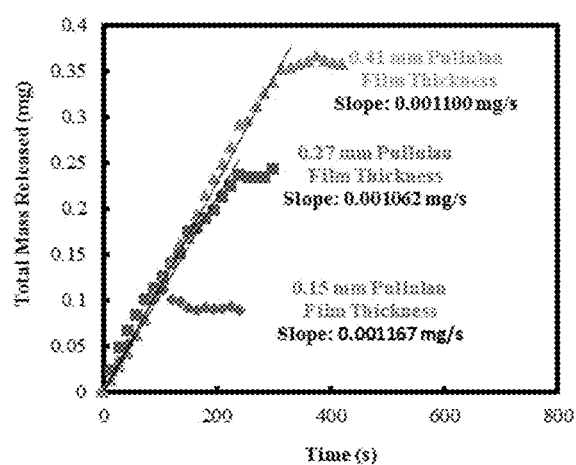
Figure 30:
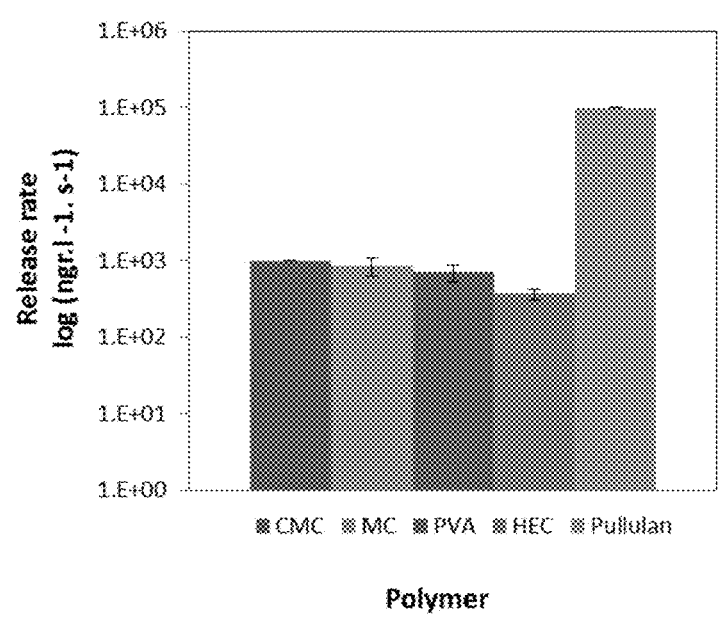

FIG. 29 shows the release kinetics for an exemplary pullulan film. Zero order kinetics are shown by the total mass of Allura Red release as a function of time FIG. 30 shows the release kinetics for different exemplary polymeric films.

Figure 31:
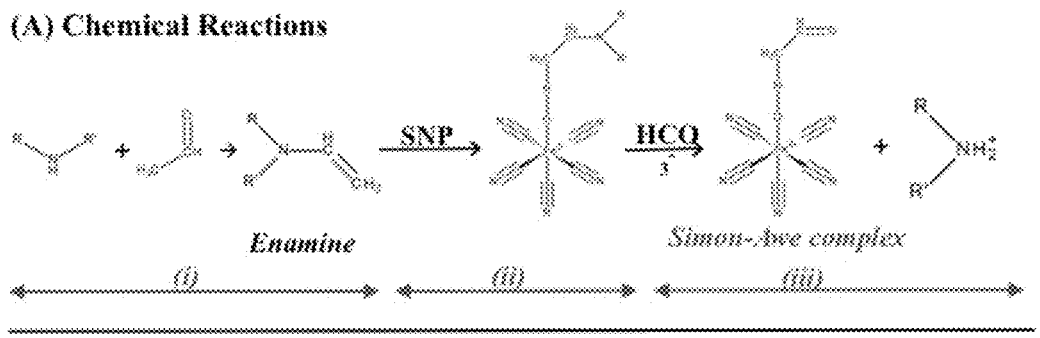
Figure 31:
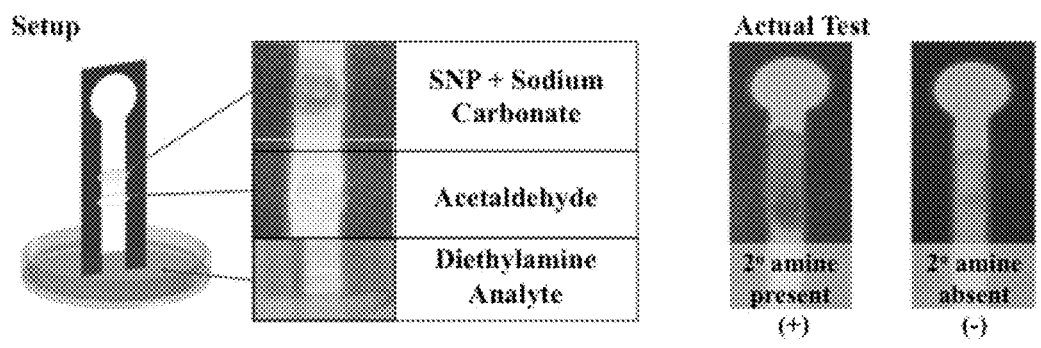
Figure 31:
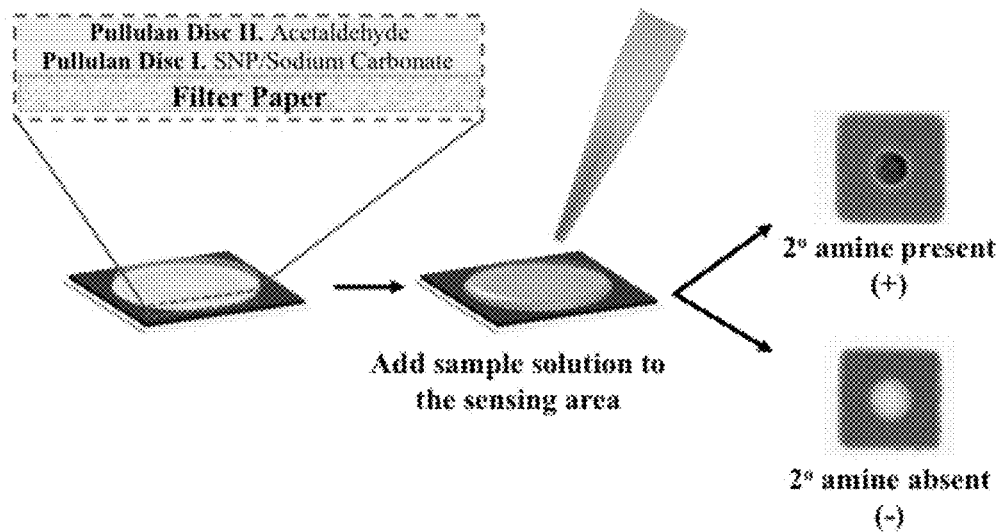

FIG. 31 shows (A) a schematic of the reactions for Simon's assay to detect secondary amines where SNP is sodium nitroprusside; (B) s schematic of the lateral flow assay for the detection of secondary amines with reagents required for the reaction immobilized in two different pullulan films. The presence of a secondary amine in the sample results in the development of a strong cobalt-blue color; and (C) a schematic of the reformatting of Simon's assay as a spot-test (z-direction), by stacking the pullulan films containing the reagents, as an exemplary sensor of the application.

Figure 32:
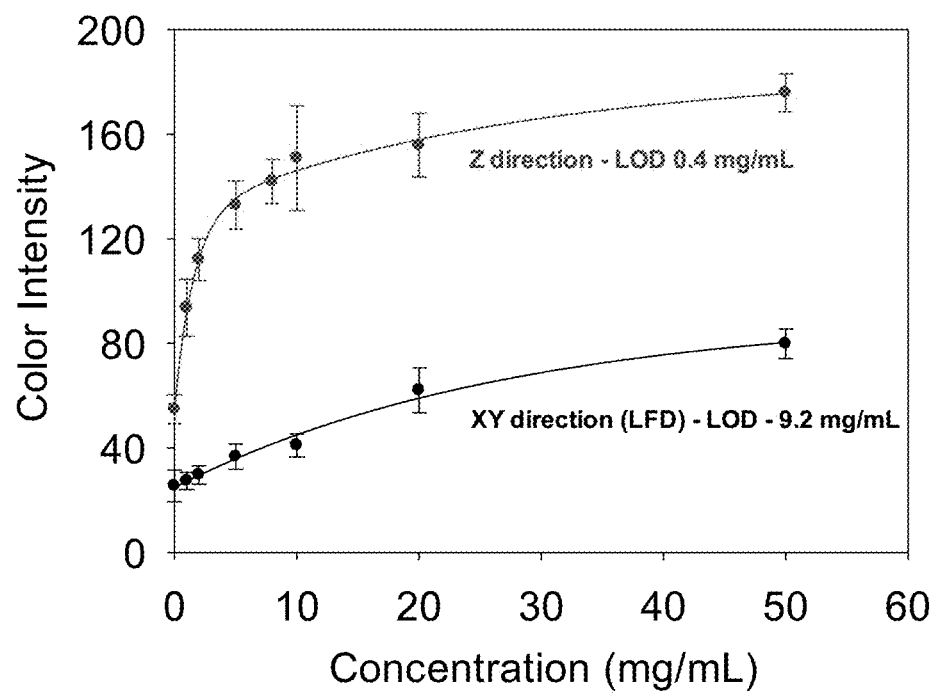

FIG. 32 shows a comparison of the color intensity for Simon's assay when performed using a lateral flow formatting (see FIG. 31B) and an exemplary z-directional format (see FIG. 31C.). The quantities of all reagents used in both formats were the same.

Figure 33:
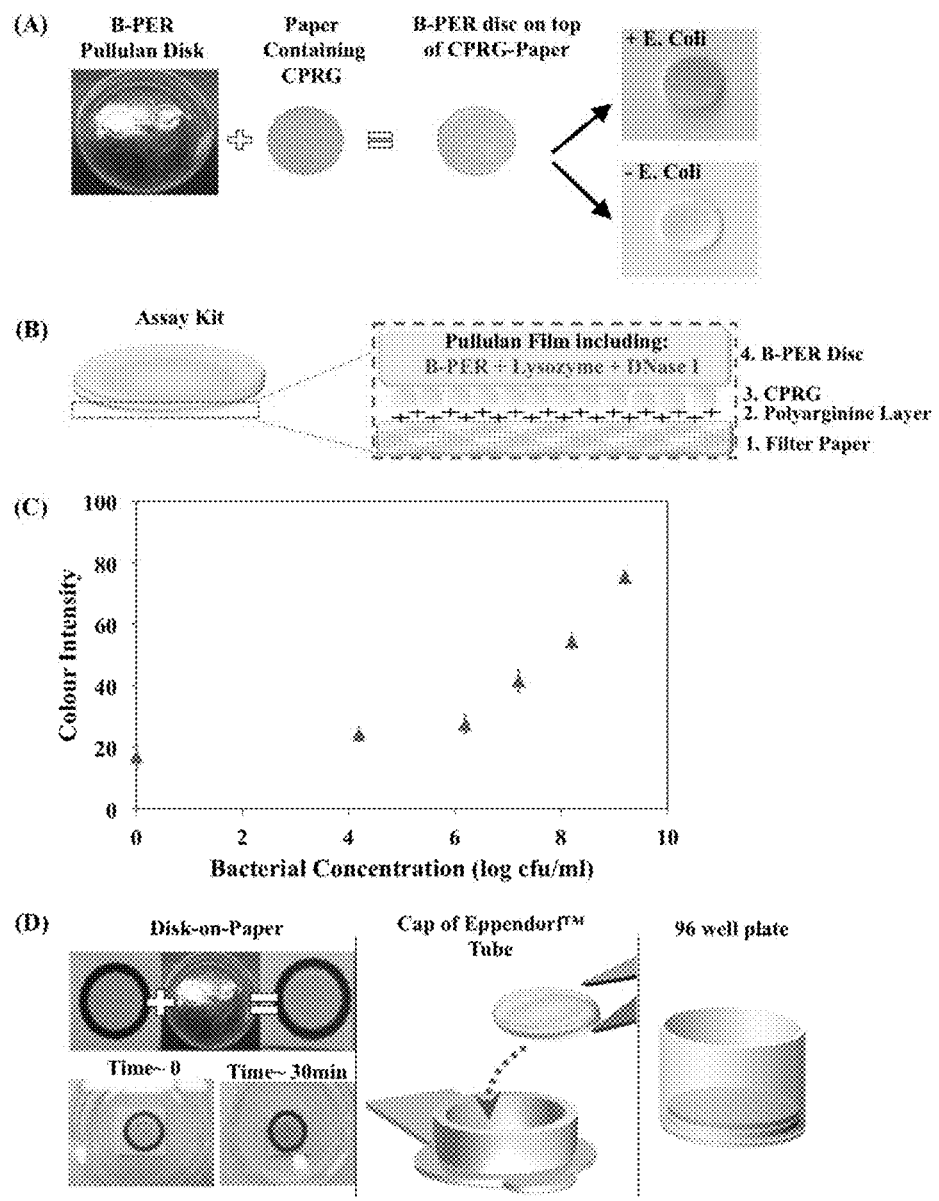

FIG. 33 shows the formatting an *E. coli* detection assay in the z-direction as an exemplary sensor of the application that allows sample preparation (cell lysis) and reporting in a without user intervention: (A) The basic components of the test comprise a pullulan film loaded with a detergent (B-PER), lysozyme and DNase I for sample extraction and a paper disk containing CPRG (the substrate for β-galactosidase) and a poly-arginine layer; (B) details of films and reagents; (C) color intensity obtained from the assay as a function of bacterial counts; and (D) multiple possibilities for formatting *E. coli* detection assay using paper disks, Eppendorf tube caps or in 96-well plates.

Figure 34:
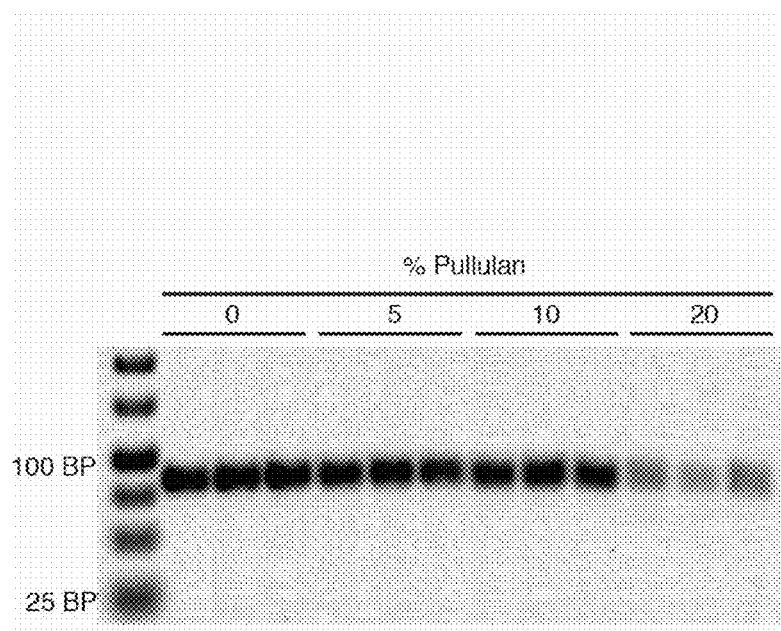

FIG. 34 shows agarose gel results of PCR products in the presence of different pullulan concentrations using exemplary sensors of the application.

DETAILED DESCRIPTION

I. Definitions

Unless otherwise indicated, the definitions and embodiments described in this and other sections are intended to be applicable to all embodiments and aspects of the present application herein described for which they are suitable as would be understood by a person skilled in the art.

In understanding the scope of the present application, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

As used in this application, the singular forms "a", "an" and "the" include plural references unless the content clearly dictates otherwise. For example, an embodiment including "a biomolecule" should be understood to present certain aspects with one biomolecule or two or more additional biomolecules.

In embodiments comprising an "additional" or "second" component, such as an additional or second biomolecule, the second component as used herein is chemically different from the other components or first component. A "third" component is different from the other, first, and second components, and further enumerated or "additional" components are similarly different.

The term "and/or" as used herein means that the listed items are present, or used, individually or in combination. In effect, this term means that "at least one of" or "one or more" of the listed items is used or present.

The term "chemical reaction" as used herein refers to any interaction between two or more molecules in which at least one of the molecules is altered. Typically at least one of the altered molecules is referred to as a "product".

The term "drying" as used herein refers to a process of allowing a solution of a polymer to cure or set until a solid, movable structure is obtained.

II. Methods of the Application

A method of performing a single step or multi-step chemical reaction comprising:
 a) combining two or more reagents for the reaction, either separately or together, with an aqueous pullulan solution to provide reagent pullulan solutions or a reagent pullulan solution, respectively;
 b) drying the reagent pullulan solutions or the reagent pullulan solution to provide solid polymeric structures or a solid polymeric structure, respectively; and
 c) if the two or more reagents are in separate solid polymeric structures in b), then treating the solid polymeric structures under conditions to dissolve the solid polymeric structures and for the reagents to interact in a chemical reaction; or
 d) if the two or more reagents are together in the solid polymeric structure in b), then treating the solid polymeric structure under conditions to dissolve the solid polymeric structure and for the reagents to interact in a chemical reaction.

In an embodiment of the application at least one of the reagents is a biomolecule. In an embodiment, the biomolecule is selected from one or more of a protein, enzyme, antibody, peptide, nucleic acid, phage, antidote and vaccine.

In embodiment, at least one of the reagents is an enzyme. In an embodiment, the enzyme is selected from DNA polymerases, restriction enzymes, DNA ligases, RNA ligases, luciferase, DNases, RNases, acetylcholine esterase, β-glucuronidase, β-galactosidase and lactate dehydrogenase. In an embodiment, the enzyme is selected from Taq DNA polymerase, phi29 DNA polymerase, Bst DNA polymerase, acetylcholine esterase, β-galactosidase, β-glucuronidase, luciferase and DNase.

In an embodiment, the nucleic acid is selected from single stranded DNA, double-stranded DNA, single-stranded RNA, double-stranded RNA, and chemically modified nucleic acid analogs in either single-stranded or double-stranded form. In an embodiment, the nucleic acid is selected from DNA aptamers, RNA aptamers, riboswitches, DNAzymes, ribozymes, SOMOmers and Spiegelmers.

In an embodiment of the application at least one of the reagents is comprised in a microorganism. In an embodiment, the microorganism is selected from one or more of anaerobic bacteria, aerobic bacteria, mammalian cells, bacterial cells and viruses.

In an embodiment of the application, at least one of the reagents is an inorganic or an organic molecule. In an embodiment, the inorganic molecule is selected from one or more of an inorganic acid, an inorganic base, an alkaline earth metal carbonate, an alkaline earth metal sulfate, an alkali metal carbonate, an alkali metal sulfate and a metal complex. In an embodiment, the inorganic molecule is a salt used in buffer solutions. In an embodiment, the organic molecule is selected from one or more of indoxyl acetate, luciferin, lactate, acetaldehyde, chelating agents, NTPs (ATP, GTP, UTP and CTP) and dNTPs (dATP, dGTP, dTTP and dCTP).

In an embodiment the reagents are selected from substances used in cell growth media, for example, but not limited to a carbon source (such as glucose), salts needed for cell growth, a source of amino acids and a source of nitrogen. A person skilled in the art would appreciate that the components of a cell growth medium will vary depending on the cell type and the particular application, but would, none-the-less, be able to select suitable components based on general knowledge in the art.

In an embodiment of the application, the conditions to dissolve the solid polymeric structure(s) comprise contacting the solid polymeric structure(s) with water or an aqueous buffer. In an embodiment, the buffer comprises tris(hydroxymethyl)aminomethane (Tris) and/or N-(2-hydroxy-1, 1-bis(hydroxymethyl)ethyl)glycine (Tricine). In a further embodiment, the conditions to dissolve the solid polymeric structure further allow the reagents to interact, via contact, in a chemical reaction.

In an embodiment of the application, the two or more reagents are in separate solid polymeric structures and the solid polymeric structures are stacked in layers on top of each other. In an embodiment, the layers are stacked in an order that corresponds to an order required to perform the chemical reaction. For example, in a multi-step chemical reaction, the reagents that interact first would be comprised in the first or top layer and/or in a solution being added to the first or top layer. Dissolution of the top polymeric structure layer results in a contacting of the reagents that interact first to provide a first reaction product. Once sufficient time has passed for the first reaction product to form, dissolution of a second pullulan layer comprising a third reagent occurs under conditions for the first reaction product to react with the third reagent to provide a second reaction product. This process can be repeated as many times as necessary to perform the entire multistep chemical reaction.

In an alternate embodiment, the two or more reagents are in separate solid polymeric structures and the solid polymeric structures are in the shape of a pill, tablet or capsule, with each separate polymeric structure forming separate layers surrounding each other in the pill. In this embodiment, the reagents that interact first would be comprised in the first or outer layer of the pill, tablet or capsule and/or in a solution being added to the first or outer layer. Dissolution of the outer polymeric structure layer results in a contacting of the reagents that interact first to provide a first reaction product. Once sufficient time has passed for the first reaction product to form, dissolution of a second pullulan layer, located internal to the outer pullulan layer and comprising a third reagent, occurs under conditions the first reaction product to react with the third reagent to provide a second reaction product. This process can be repeated as many times as necessary to perform the entire multistep chemical reaction. Accordingly, in this embodiment of the application, the layer on the outside of the pill, tablet or capsule comprises reagents that must react first in the chemical reaction and the remaining layers are arranged inside the outside layer in an order that corresponds to an order required to perform the chemical reaction.

In an embodiment, the two or more reagents are in separate polymeric structures and the two or more reagents that are in separate polymeric structures comprise an enzyme or a receptor and a substrate for the enzyme or the receptor. In a further embodiment, dissolving a first polymeric structure in the presence of a test sample that is suspected of comprising a modulator of the receptor or enzyme, followed by dissolution of a second polymeric structure comprising a substrate for the enzyme or receptor is used in a method of assaying for modulators of, or molecules that bind to, the enzyme or receptor. In this embodiment, if the final product of the chemical reaction differs in the presence of the test sample compared to in the presence of a control (i.e. a sample comprising no suspected modulator or binder) then the test sample comprises a modulator of, or a molecule that binds to, the receptor or enzyme. In an embodiment, the final product of the chemical reaction in the presence of the test sample or the final product of the chemical reaction in the absence of the test sample is detectable using any known method. For example, the product is detectable using colormetry, optical spectrometry and/or fluorescence.

Non-limiting examples of known enzymes and their known substrates and detection systems that are amenable to adaptation and use in the method of the present application are as follows:
  (i) Acetylcholine esterase—acetylthiocholine/dithiobisnitrobenzoate (DTNB);
  (ii) Acetylcholine esterase—indophenyl acetate or indoxyl acetate;
  (iii) urokinase plasminogin activator (uPA)—S-2244;
  (iv) adenosine triphosphatases (ATPases)/kinases—ATP-βS/DTNB;
  (v) β-glucuronidase—5-bromo-4-chloro-3-indolyl-β-D-glucuronide (X-GLUC)/FeCl$_3$/indigo dye;
  (vi) β-galactosidase—bromo-chloro-indolyl-galactopyranoside (X-GAL)/indigo dye
  (vii) DNA/RNA/PNA aptamers, DNA/RNA enzymes or a DNA or RNA aptazyme/signaling method;
  (viii) functional nucleic acid/Φ29 DNA polymerase/Bst DNA polymerase, circular template and dNTPs/gold nanoparticle labeled linear DNA of the same sequence as the circular template (or a portion thereof).

In an embodiment, the two or more reagents that are in separate polymeric structures comprise AChE and indoxyl acetate.

In an embodiment, the two or more reagents that are in separate polymeric structures comprise (1) reagents for cell lysis and (2) a substrate for an enzyme that is released from a cell in the presence of the reagents for cell lysis. In an embodiment, the reagents for cell lysis are selected from one or more of detergents, lysozyme, lytic bacteriophage and DNase I. In a further embodiment, the enzyme that is released from a cell in the presence of the reagents for cell lysis is β-galactosidase or β-glucuronidase. In a further embodiment, the substrate for the enzyme is selected from 5-bromo-4-chloro-3-indolyl-β-D-glucuronide (X-GLUC), bromo-chloro-indolyl-galactopyranoside (X-GAL), 5-bromo-3-indolyl β-D-galactopyranoside (Bluo-Gla), 5-bromo-6-chloro-3-indolyl β-D-galactopryaniside (Magenta-Gal), 6-chloro-3-indolyl β-D-galactopyranoside (Salmon-Gal), 2-nitrophenyl β-D-galactopyranoside (ONPG) and 4-nitro β-D-galactopyranoside (PNPG).

In an embodiment, the two or more reagents that are in separate polymeric structures comprise the reagents to perform the Simon's test for secondary amines. In this embodiment, the top or first layer in a stacked sensor, or the first or outer layer of a pill, tablet or capsule, comprises acetaldehyde and the second or inner layer comprises sodium nitroprusside and sodium carbonate. To perform the method of the application, the top layer of a stack of solid polymeric structures or the outer layer of a pill, tablet or capsule is contacted with an aqueous solution that is suspected of comprising a secondary amine. If the blue color of the Simon-Awe complex is detected, then the sample comprised a secondary amine.

It is an embodiment of the application that timing of dissolution of the layers, whether stacked or in a pill, tablet or capsule, is controlled to allow sufficient reaction time for each step of the chemical reaction. In an embodiment, the timing is controlled by one or more of thickness of the layers and pullulan concentration.

In an embodiment of the application, the two or more reagents are in the same solid polymeric structure. In this embodiment, the solid polymeric structure is optionally referred to as an "all-in-one" pill, tablet capsule or film.

In an embodiment, the two or more reagents in the same solid polymeric structure comprise reagents for detection of adenosine triphosphate (ATP). In an embodiment the reagents for ATP detection comprise luciferin, luciferase, coenzyme A (CoA), dithiothreitol (DTT), a chelating reagent, MgCO$_3$ and MgSO$_4$. In an embodiment, the chelating agent is ethylenediaminetetraacetic acid (EDTA).

In another embodiment, the two or more reagents in the same solid polymeric structure comprise reagents for rolling circular amplification (RCA). In a embodiment, the reagents for RCA comprise DNA polymerase (such as phi29 DNA polymerase), circular template DNA and buffer salts.

In another embodiment, the two or more reagents in the same solid polymeric structure comprise reagents for cell growth media. In an embodiment, reagents for cell growth media comprise carbon source (such as glucose), salts needed for cell growth, a source of amino acids and a source of nitrogen.

In another embodiment, the two or more reagents in the same solid polymeric structure comprise reagents for PCR. In an embodiment, the reagents for PCR comprise DNA polymerase (for example Taq DNA polymerase_, linear template DNA and buffer salts.

In the above "all-in-one" embodiments, the present application provides the advantage of having many or all of the reagents required for a chemical reaction, such as, but not limited to, cell growth, nucleic acid amplification, and ATP detection, in a single stable solid polymeric structure that is readily stored and transported. The reagents are optionally, premeasured and/or stabilizing reagents, such as antibiotics, are added.

In an embodiment of the application, the two or more reagents are in separate solid polymeric structures and the solid polymeric structures are each dissolved in a single water or buffer solution releasing the reagents for interaction in the chemical reaction. In this embodiment, it is a further embodiment that the solid polymeric structures are, independently, in a shape selected from a pill, tablet and capsule.

It is an embodiment that the amount of the two or more reagents that are combined with the aqueous pullulan solution is premeasured. In an embodiment, the premeasured amount corresponds to amounts and ratios of reagents needed to perform the chemical reaction(s). In a further embodiment, stabilizing agents, such as antimicrobial agents, are included in the aqueous pullulan solution.

In an embodiment, the chemical reaction produces a product that is detectable using any known method. For example, the product is detectable using colormetry, optical spectrometry and/or fluorescence.

In an embodiment, the concentration of the aqueous pullulan solutions is about 5% (w/v) to about 25% (w/v). In a further embodiment, the concentration of the aqueous pullulan solutions is about 10% (w/v) to about 20% (w/v). In a further embodiment, the concentration of the aqueous pullulan solutions is about 11% (w/v) to about 13% (w/v), or about 12% (w/v).

In an embodiment of the application the one or more of solid polymeric structures is cast onto a substrate comprising at least one reagent for the chemical reaction. In this embodiment, dissolution of the solid polymeric structure on the substrate brings the reagent(s) in the solid polymeric structure into contact with the reagent(s) on and/or in the substrate to interact in a chemical reaction. In an embodiment, the substrate is a paper-based substrate. In a further embodiment, the substrate is surface treated with the at least one reagent for the reaction.

III. Sensors and Devices of the Application

The present application also includes sensors or devices comprising two or more reagents entrapped in the same solid polymeric structure or in different solid polymeric structures wherein the solid polymeric structure(s) are comprised of pullulan. In an embodiment, at least one of the two or more reagents is a biomolecule and the sensor is a biosensor.

In an embodiment, the biomolecule is selected from one or more of a protein, enzyme, antibody, peptide, nucleic acid, phage, antidote and vaccine. In an embodiment, at least one of the reagents is an enzyme. In an embodiment, the enzyme is selected from DNA polymerases, restriction enzymes, DNA ligases, RNA ligases, luciferase, DNases, RNases, acetylcholine esterase, β-glucuronidase, β-galactosidase and lactate dehydrogenase. In an embodiment, the enzyme is selected from Taq DNA polymerase, Φ29 DNA polymerase, Bst DNA polymerase, acetylcholine esterase, β-galactosidase, β-glucuronidase, luciferase and DNase. In an embodiment, the nucleic acid is selected from single stranded DNA, double-stranded DNA, single-stranded RNA, double-stranded RNA, and chemically modified nucleic acid analogs in either single-stranded or double-stranded form. In an embodiment, the nucleic acid is selected from DNA aptamers, RNA aptamers, riboswitches, DNAzymes, ribozymes, SOMOmers and Spiegelmers.

In an embodiment of the application at least one of the reagents is comprised in a microorganism. In an embodiment, the microorganism is selected from one or more of anaerobic bacteria, aerobic bacteria, mammalian cells, bacterial cells and viruses.

In an embodiment of the application, at least one of the reagents is an inorganic or an organic molecule. In an embodiment, the inorganic molecule is selected from one or more of an inorganic acid, an inorganic base, an alkaline earth metal carbonate, an alkaline earth metal sulfate, an alkali metal carbonate, an alkali metal sulfate and a metal complex. In an embodiment, the inorganic molecule is a salt used in buffer solutions. In an embodiment, the organic molecule is selected from one or more of indoxyl acetate, luciferin, lactate, acetaldehyde, chelating agents, NTPs (ATP, GTP, UTP and CTP) and dNTPs (dATP, dGTP, dTTP and dCTP).

In an embodiment the reagents are selected from substances used in cell growth media, for example, but not limited to a carbon source (such as glucose), salts needed for cell growth, a source of amino acids and a source of nitrogen. A person skilled in the art would appreciate that the components of a cell growth medium will vary depending on the cell type and the particular application, but would, none-the-less, be able to select suitable components based on general knowledge in the art.

In an embodiment of the application, the two or more reagents are in separate solid polymeric structures and the solid polymeric structures are stacked in layers on top of each other. In an embodiment, the layers are stacked in an order that corresponds to an order required to perform the chemical reaction. For example, in a multi-step chemical reaction, the reagents that interact first would be comprised in either the first or top layer and/or in a solution being added to the first or top layer.

In an alternate embodiment, the two or more reagents are in separate solid polymeric structures and the solid polymeric structures are in the shape of a pill, tablet or capsule, with each separate polymeric structure forming separate layers surrounding each other in the pill. In this embodiment, the reagents that interact first would be comprised in either the first or outer layer of the pill, tablet or capsule and/or in a solution being added to the first or outer layer. Dissolution of the outer polymeric structure layer results in a contacting of the reagents that interact first to provide a first reaction product. Once sufficient time has passed for the first reaction product to form, dissolution of a second pullulan layer, located internal to the outer pullulan layer and comprising a third reagent, occurs under conditions for the first reaction product to react with the third reagent to provide a second reaction product. Accordingly, in this embodiment of the application, the layer on the outside of the pill, tablet or capsule comprises reagents that must react first in the chemical reaction and the remaining layers are arranged inside the outside layer in an order that corresponds to an order required to perform the chemical reaction.

In an embodiment, the two or more reagents are in separate polymeric structures and the two or more reagents that are in separate polymeric structures comprise an enzyme or a receptor and a substrate for the enzyme or the receptor. Non-limiting examples of known enzymes and their known substrates and detection systems that are amenable to adaptation and use in the method of the present application are as follows:

(i) Acetylcholine esterase—acetylthiocholine/dithiobisnitrobenzoate (DTNB);
(ii) Acetylcholine esterase—indophenyl acetate or indoxyl acetate;
(iii) urokinase plasminogin activator (uPA)—S-2244;
(iv) adenosine triphosphatases (ATPases)/kinases—ATP-βS/DTNB;
(v) β-glucuronidase—5-bromo-4-chloro-3-indolyl-β-D-glucuronide (X-GLUC)/FeCl$_3$/indigo dye;
(vi) β-galactosidase—bromo-chloro-indolyl-galactopyranoside (X-GAL)/indigo dye
(vii) DNA/RNA/PNA aptamers, DNA/RNA enzymes or a DNA or RNA aptamzyme/signaling method;
(viii) functional nucleic acid/Φ29 DNA polymerase/Bst DNA polymerase, circular template and dNTPs/gold nanoparticle labeled linear DNA of the same sequence as the circular template (or a portion thereof).

In an embodiment, the two or more reagents that are in separate polymeric structures comprise AChE and indoxyl acetate.

In an embodiment, the two or more reagents that are in separate polymeric structures comprise (1) reagents for cell lysis and (2) a substrate for an enzyme that is released from a cell in the presence of the reagents for cell lysis. In an embodiment, the reagents for cell lysis are selected from one or more of detergents, lysozyme, lytic bacteriophage and DNaseI. In a further embodiment, the enzyme that is released from a cell in the presence of the reagents for cell lysis is β-galactosidase or β-glucuronidase. In a further embodiment, the substrate for the enzyme is selected from 5-bromo-4-chloro-3-indolyl-β-D-glucuronide (X-GLUC), bromo-chloro-indolyl-galactopyranoside (X-GAL), 5-bromo-3-indolyl β-D-galactopyranoside (Bluo-Gla), 5-bromo-6-chloro-3-indolyl β-D-galactopryaniside (Magenta-Gal), 6-chloro-3-indolyl β-D-galactopyranoside (Salmon-Gal), 2-nitrophenyl β-D-galactopyranoside (ONPG) and 4-nitro β-D-galactopyranoside (PNPG).

In an embodiment, the two or more reagents that are in separate polymeric structures comprise the reagents to perform the Simon's test for secondary amines. In the embodiment, the top or first layer in a stacked sensor, or the first or outer layer of a pill, tablet or capsule comprises acetaldehyde and the second or inner layer comprises sodium nitroprusside and sodium carbonate.

It is an embodiment of the application that timing of dissolution of the layers, whether stacked or in a pill, tablet or capsule, is controlled to allow sufficient reaction time for each step of the chemical reaction. In an embodiment, the timing is controlled by one or more of thickness of the layers and pullulan concentration.

In an embodiment of the application, the two or more reagents are in the same solid polymeric structure. In this embodiment, the solid polymeric structure is optionally referred to as an "all-in-one" pill, tablet capsule or film.

In an embodiment, the two or more reagents in the same solid polymeric structure comprise the reagents for detection of adenosine triphosphate (ATP). In an embodiment the reagents for ATP detection comprise luciferin, luciferase, coenzyme A (CoA), dithiothreitol (DTT), a chelating reagent, MgCO$_3$ and MgSO$_4$.

In another embodiment, the two or more reagents in the same solid polymeric structure comprise reagents for rolling circular amplification (RCA). In a embodiment, the reagents for RCA comprise DNA polymerase (such as phi29 DNA polymerase), circular template DNA and buffer salts.

In another embodiment, the two or more reagents in the same solid polymeric structure comprise reagents for cell growth media. In an embodiment, reagents for cell growth media comprise carbon source (such as glucose), salts needed for cell growth, a source of amino acids and a source of nitrogen.

In another embodiment, the two or more reagents in the same solid polymeric structure comprise reagents for PCR. In an embodiment, the reagents for PCR comprise DNA polymerase (such as Taq DNA polymerase), linear template DNA and buffer salts.

In the above "all-in-one" embodiments, the present application provides the advantage of having many or all of the reagents required for a chemical reaction, such as, but not limited to, cell growth, nucleic acid amplification, and ATP detection, in a single stable solid polymeric structure that is readily stored and transported. The reagents are optionally, premeasured and/or stabilizing reagents, such as antibiotics, are added.

In an embodiment of the application, the two or more reagents are in separate solid polymeric structures and the solid polymeric structures are each dissolved in a single water or buffer solution releasing the reagents for interaction in the chemical reaction. In this embodiment, it is a further embodiment that the solid polymeric structures are, independently, in a shape selected from a pill, tablet and capsule.

It is an embodiment that the amount of the two or more reagents that are combined with the aqueous pullulan solution are premeasured. In an embodiment, the premeasured amount corresponds to amounts and ratios of reagents needed to perform the chemical reaction(s). In a further embodiment, stabilizing agents, such as antimicrobial agents, are included in the solid polymeric structure(s).

In an embodiment, the chemical reaction produces a product that is detectable using any known method. For example, the product is detectable using colormetry, optical spectrometry and/or fluorescence. Accordingly, in an embodiment of the application the sensors comprise a detection device.

In an embodiment of the application the one or more of solid polymeric structures is cast onto a substrate comprising at least one reagent for the chemical reaction. In this embodiment, dissolution of the solid polymeric structure on the substrate brings the reagent(s) in the solid polymeric structure into contact with the reagent(s) on and/or in the substrate to interact in a chemical reaction. In an embodiment, the substrate is a paper-based substrate. In a further embodiment, the substrate is surface treated with the at least one reagent for the reaction.

In an embodiment, the solid polymeric structures comprise about 5% (w/v) to about 25% (w/v) of the pullulan. In a further embodiment, the solid polymeric structures comprise about 10% (w/v) to about 20% (w/v) of the pullulan. In a further embodiment, the solid polymeric structures comprise about 11% (w/v) to about 13% (w/v), or about 12% (w/v), of the pullulan.

In an embodiment, the sensors and devices of the application are comprised in commercial kits for performing the desired chemical reaction(s).

The following are specific, non-limiting examples of some sensors and devices of the present application:
(a) AChE Sensors
A sensor for the detection of inhibitors of acetylcholine esterase (AChE) comprising:
a) a pullulan polymeric structure comprising the AChE; and
b) a pullulan polymeric structure comprising indole acetic acid (IDA), wherein a) and b) are arranged so that a) is first contacted with a sample comprising one or more test substances under conditions to dissolve the pullulan polymeric structure and for the one or more test substances and the AChE to interact to provide a first reaction solution followed by contacting b) with the first reaction solution.

In an embodiment of the application, the pullulan polymeric structure in a) is a film on the inner wall of a reaction vessel and the pullulan polymeric structure in b) is a pill, capsule or tablet.

In an embodiment of the application the sensor for the detection of inhibitors of acetylcholine esterase is a layered pill, tablet or capsule wherein the pullulan polymeric structure in a) forms an outer layer and the pullulan polymeric structure in b) forms an inner layer.

In an embodiment, the outer and inner layers are adjacent and contacting each other.

In an embodiment of the application, the pullulan polymeric structure in a) and the pullulan polymeric structure in b) are both films that are stacked in layers adjacent and contacting each other.

In an embodiment of the application, the timing of the dissolution of the layers is controlled to allow sufficient time for the one or more test substances and the AChE to interact to provide a first reaction solution. In an embodiment, the timing is controlled by one or more of thickness of the layers and pullulan concentration.

In an embodiment, the pullulan polymeric structure in a) and the pullulan polymeric structure in b) are cast in two separate structures that are added sequentially to the sample comprising one or more test substances, with the pullulan polymeric structure in a) being added to the sample prior to the pullulan polymeric structure in b), and wherein the pullulan polymeric structure in b) is added to the sample when the pullulan polymeric structure in a) has dissolved and the one or more test substances and the AChE have interacted to provide the first reaction solution.

(b) β-Galactosidase Sensors

It has been demonstrated herein that stacked pullulan films with various reagents can be used to perform multi-step reactions in a single step to produce sensor outputs based on complex reaction sequences. In addition, such reactions can utilize labile and/or volatile reagents, as these remain intact and immobilized when present in pullulan films. The arrangement and thickness of the stacked films can be varied to control reaction timing and sequence, or incorporate delays for sample preparation or incubation prior to detection steps. This time dependent reagent deliverer allows the user to manipulate fluid movement in all three directions (x, y and z directions) to create multi-step reactions and assays. Using this technology, paper based analytical devices were created for the detection of secondary amines a methamphetamine mimic (DEA) and a fecal coliform (*E. coli* O157). These sensors avoided previously required sample handling steps, such as cell lysis, and thus simplified the assays. Given the dual benefits of reagent stabilization and controlled release, this format should be amenable to a wide range of complex sequential reactions on paper-based microanalytical devices.

Accordingly, the present application includes a sensor for the detection of β-galactosidase activity from a microorganism comprising:
  a) a pullulan polymeric film comprising a detergent, lysozyme and DNase I; and
  b) a substrate surface treated with chlorophenol red β-D-galactopyranoside (CPRG), and optionally, polyarginine, wherein a portion of b) is coated with the pullulan polymeric film of a).

(c) Secondary Amine Sensors

The present application also includes a sensor for the detection of secondary amines comprising
  a) a pullulan polymeric structure comprising acetaldehyde; and
  b) a pullulan polymeric structure comprising sodium nitroprusside and sodium carbonate, wherein a) and b) are arranged so that a) is first contacted with a sample comprising one or more test substances under conditions to dissolve the pullulan polymeric structure and for the one or more test substances and the acetaldehyde to interact to provide a first reaction solution followed by contacting b) with the first reaction solution.

In an embodiment of the application, the pullulan polymeric structure in a) and the pullulan polymeric structure in b) are both films that are stacked in layers adjacent and contacting each other.

In an embodiment of the application, the timing of the dissolution of the layers is controlled to allow sufficient time for the one or more test substances and the acetaldehyde to interact to provide a first reaction solution. In an embodiment, the timing is controlled by one or more of thickness of the layers and pullulan concentration.

(d) ATP Detection

A highly strenuous and time-consuming luminescence assay was made single-step by encapsulating all the reagents, including highly unstable enzyme and substrate in a single pill using pullulan. All the components were thermally stable in the pills which provided sensitive ATP detection up to picomolar concentration. This cost-effective method (~88 Canadian cents per 100 pills which is up to 130 times cheaper than the solution-based commercial assay kits), is also easy to scale-up. This stabilization technique will cover a broad spectrum of application ranging from inexpensive real-time ATP testing to high-throughput screening applications where sensitivity and stable light emission are desired.

Accordingly, the present application also includes a sensor for ATP detection comprising all reagents for ATP detection in a pullulan polymeric structure. In an embodiment, the reagents for ATP detection comprise luciferin, luciferase, coenzyme A (CoA), dithiothreitol (DTT), a chelating reagent, $MgCO_3$ and $MgSO_4$.

(e) Nucleic Acid Amplification

The present application also includes a device for amplifying DNA using PCR comprising a pullulan polymeric structure comprising DNA polymerase (such as Taq DNA polymerase), linear template DNA and buffer salts. The present application also includes a device for amplifying DNA using RCA comprising a pullulan polymeric structure comprising DNA polymerase (such as phi29 DNA polymerase), linear template DNA and buffer salts. In an embodiment, the device is in the form of a tablet, pill or capsule.

(f) Cell Growth Media

The present application also includes a device for transporting cell growth media comprising a pullulan polymeric structure comprising reagents for cell growth media. In an embodiment, reagents for cell growth media comprise carbon source (such as glucose), salts needed for cell growth, a source of amino acids and a source of nitrogen.

EXAMPLES

The following non-limiting examples are illustrative of the present application:

Example 1: Pullulan Encapsulated Enzyme/Substrate

Figure 1A:
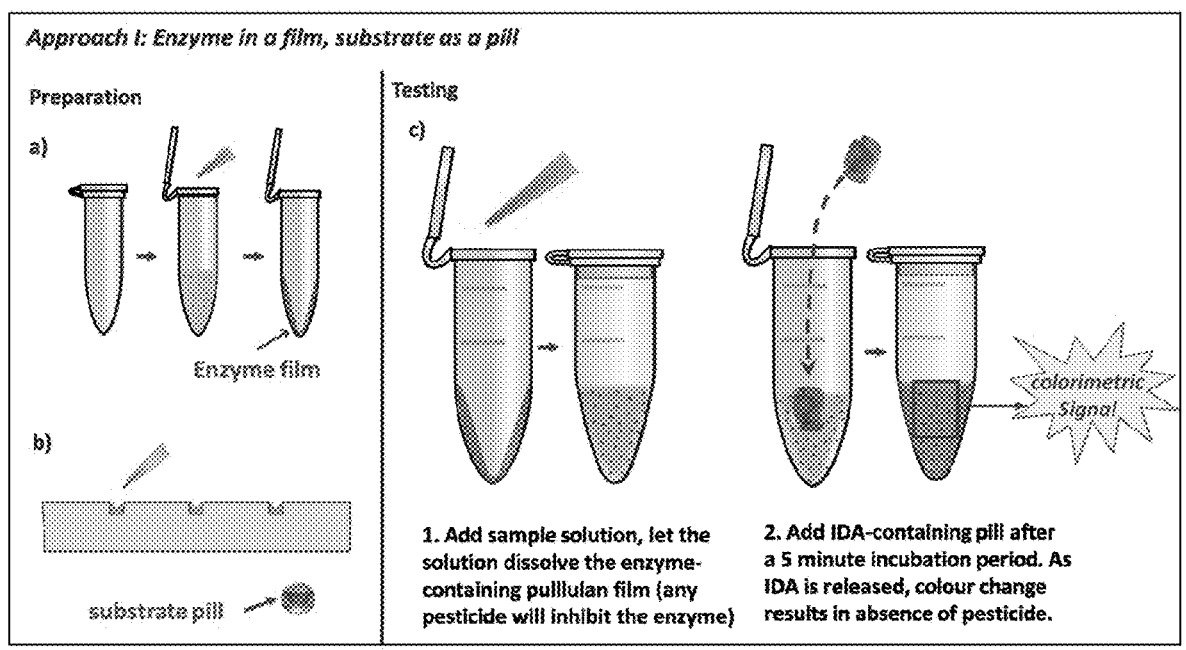

It is suggested that, since paper is very non-uniform and cannot be counted on for reliable results, to remove the paper from a sensing system. This could be accomplished by creating pullulan capsules which shows high oxygen barrier properties while it is a fast dissolvable polymer. Here in two separate parts, are first explained the methods of creating capsules in different shape and sizes, then the idea of creating a lab on a capsule, particularly the pesticide detection sensor, is explored. Two approaches are considered for creating the pesticide sensor (see FIGS. 1A and 1B): Approach I) Two separate pills: Pullulan/Enzyme film is casted inside of an Eppendorf tube, while IDA is separately entrapped in a pullulan pill. In this case the sensor operation method would be: First 200 µl of the water sample is added to the Eppendorf tube which its inner wall is covered with previously casted AChE-pullulan, after around 5 minutes allowing incubation of the released enzyme, then the IDA-pullulan pill is dropped into the tube and let it to be released and react with un-inhibited enzyme to developed color. Approach II) Unique capsule: the IDA-pullulan pill is encapsulated inside a AChE-pullulan capsule. So as the result, when the capsule is dropped to the sample solution, it starts to dissolve the outer layer of the capsule which includes the enzyme (AChE) in approximately 5 minutes allowing incubation of the released enzyme. The sample solution then dissolves the inner capsule allowing the substrate to be released and react with un-inhibited enzyme to developed color.

(a) Pullulan Capsules

Figure 2:
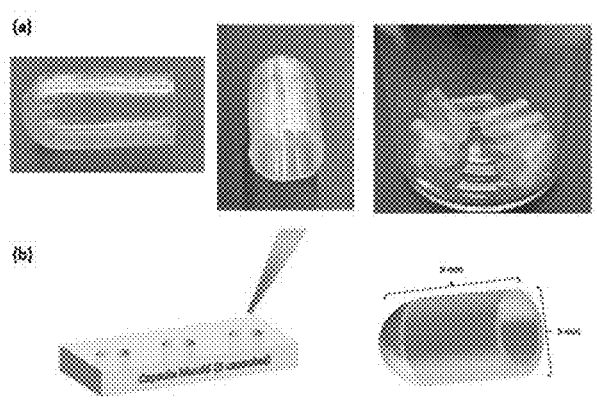

To make the capsules, 100 mg of pullulan was dissolved in 1 mL of dH$_2$O, and 200 µL of the resulting solution was added to a prepared mold (3 capsules at a time). This mold was then allowed to dry for approximately 22 hours, followed by 2 hours in the oven at about 75° C. to complete the drying process. The capsules were cast into the smaller holes in the mold, while the larger holes were used to cast a large capsule, which required 270 µL of the solution. FIG. 2 contains images of the completed capsules.

Casting Capsules (Different Sizes)

Figure 3:
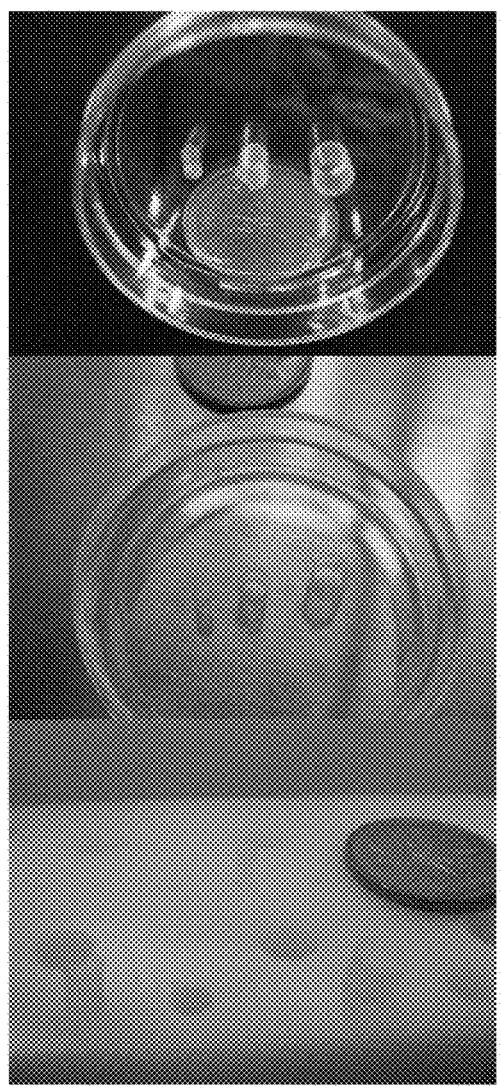

Different size capsules (pullulan) were tested. These capsule sizes were: 2 mm, 3 mm, 4 mm and 5 mm respectively (diameter). The depth of all capsules was 4 mm. These molds were filled with pullulan solution of 100 mg/mL, 200 mg/mL and 300 mg/mL respectively, and allowed to dry overnight. The resulting capsules revealed that the 100 mg/mL was too thin to be of practical use, and the 300 mg/mL was very difficult to remove from the mold. However, the 200 mg/mL returned very good capsules as pictured in FIG. 3.

Figure 4:
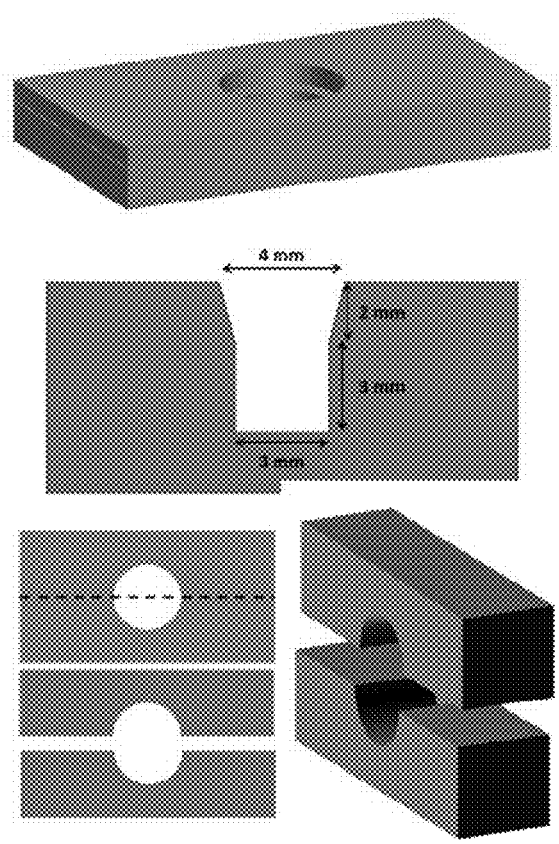

It was decided to cast capsules in different formats, so as to allow for easy release of the capsules, as well as a capsule shape that more easily allows for sealing the top on. The methods investigated are shown in FIG. 4. Additionally, it was observed that if the capsule mold was warmed up to ~70° C. after the capsules were dried, the holes expand and allow for easy release of the capsule.

Sealing Capsules while in Mold

It is also suggested that it may be easier to seal the capsules inside the mold, as the mold would hold the capsule in the right orientation and perhaps allow for an easier application of the film.

A modification of this idea was to seal the capsules after making a custom-sized hole in a Styrofoam block to support the capsule while it is sealed. This worked quite well.

Casting Under a Nitrogen Blanket

It is attempted to remedy the issue of poor enzyme maintenance by casting the films under a nitrogen blanket, which should prevent enzyme oxidation as a result of recirculation during the casting procedure. To serve as a control, a film is also cast in the bio safety cabinet simultaneously, where it is in contact with oxygen during the casting procedure. Another film is cast in a beaker containing a plastic petri dish with a brass ring with a constant supply of nitrogen gas a low pressure/flow rates.

Casting Pullulan Capsules

Several capsules were cast in which 75 µL of 300 mg/mL plain pullulan solution was added to the caps of small eppendorf (microcentrifuge) tubes. These capsules were then left for 2 days to allow for complete drying (in a fume hood).

In order to compare the functionality of pullulan vs. polyvinyl alcohol (PVA) in a capsular format, 10 capsules were also cast of PVA. Since PVA is a much denser solution, only 100 mg/mL solution was used.

PVA Capsule Casting and Testing

Some capsules were formed from PVA to test if it is a viable alternative (much cheaper) to pullulan. 75 µL of 150 mg/mL PVA was cast into Eppendorf microcentrifuge tube caps. The resulting capsules were found to be very easy to remove from the mold, did not dissolve in ethanol, and were (slowly) soluble in water. These are desirable characteristics of the polymer. A 5 mL film of PVA was also cast (3.5 cm Falcon petri dish, 5 mL volume of 50 mg/mL PVA solution), and capsules were formed on a glass surface using the brass rings (microscope slide glass (smooth) and ½" brass casting rings). The resulting capsules were then tested to determine solubility. PVA capsules and films were colorless and flexible (more so than pullulan).

However, the PVA was much slower to dissolve to form a solution, and typically required the application of heat (~80° C.) on a magnetic stir plate. When the PVA solution was prepared using microfuge tubes and the vortex, a foam was created that did not go away, rendering the solution useless.

Several of the PVA capsules were used to determine if they were applicable to the encapsulation of smell enzymes, and tested with skunk oil dissolved in methanol. The methanol resulted in the capsule becoming very flexible and it contracted, not sealing properly.

Dissolution of PVA Capsules

In order to test how long the PVA capsules take to release a dye, several milligrams of Allura Red dye (in powder form) was added to the inside of several 100 mg/mL PVA capsules, and the top was sealed with a PVA glue solution and a 5 mL (50 mg/mL) 3.5 cm cast film punched to 5/32". The sealed capsules were then washed with ethanol, and added to 100 uL of dH$_2$O to determine how long it takes for the dye to be released. The results indicated that the release time is between 2 min and 4 min 10 sec. For a reliable inactivation of the AChE by any pesticide in a sample solution, a minimum incubation period of ~6 minutes is required, hence the PVA capsules (unless cast thicker) will not function as a release mechanism.

Example 2: Pesticide Sensor Capsules

It is suggested that in a paper-based sensor, since the paper is very non-uniform and cannot be counted on for reliable results, to remove the paper from the sensing system. This could be accomplished by creating pullulan capsules, as previously described, and nesting two capsules together, as demonstrated in FIG. 4.

Figure 5:
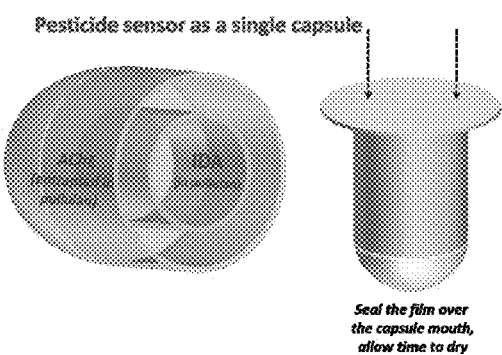
FIG. 5 shows a schematic diagram of a proposed exemplary paper-less pesticide sensor relying on the enzyme (AChE) and substrate (IDA), as well as a side view of one of the proposed exemplary capsules and method of sealing.
Figure 6:
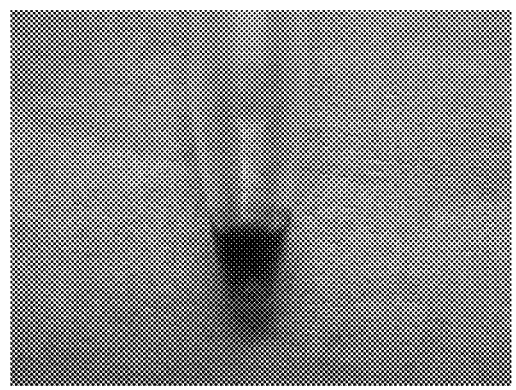
FIG. 6 shows the bluish green color change (dark) exhibited after 24 hours of oxygen exposure in an exemplary sensor of the application. 5 μL of AChE, 5 μL of IDA and 35 μL of dH$_2$O were added. The AChE was cast into the bottom of the tube in 50 μL of a solution of 125 mg/mL pullulan.

As can be seen from FIG. 5, the outermost pullulan capsule layer will dissolve first, when contacted with an aqueous sample. The pullulan capsule should be thin enough to allow for rapid dissolution. If there are any pesticides present in the water, the pesticides will rapidly inactivate the enzyme. Approximately a 5 minute incubation period is desirable. During this time, the inner capsule (containing IDA) should not dissolve. Therefore, the capsule may be composed of:
  i. a thicker layer of pullulan that will resist complete dissolution for about 5 minutes
  ii. a thinner layer of another, slower-to-dissolve polymer that can be cast into a capsule shape using the same method.

Figure 1B:
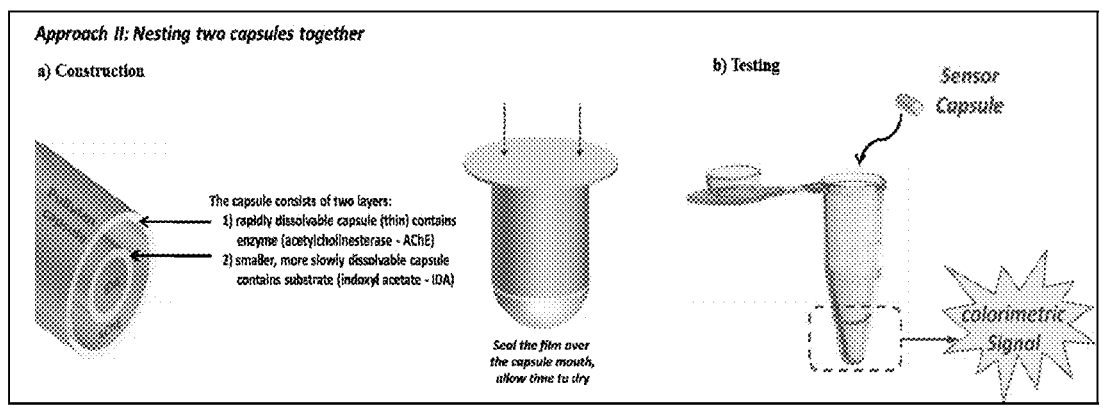

The basic construction process for the capsules has already been introduced, as demonstrated in FIG. 1B. In order to create 'nested' capsules, two capsules of different sizes are cast.

An issue with this type of sensor is the sample size. If a very large volume is used, the AChE enzyme will dissipate, especially if some convective currents occur, or non-stagnant sample is used. In this case, by the time the 5 minute capsule inside has dissolved, the IDA will not come into contact with enough AChE in a small enough area to result in any visible color change.

It is suggested to use a sample container which possesses a known volume (relatively small). The resultant color intensity of the liquid sample after a certain time frame (should be ~6 minutes) can be used to form a standard curve against pesticide concentration, and the device should be able to be used as a quantifiable sensor. For a qualitative sensor only, any blue color change should be clear enough to identify in a small volume, particularly if the color of the container is selected so as to maximize the contrast between any blue color and the background color.

As a starting point, the film or capsules that encapsulate the IDA and the enzyme-containing films as well are created, as a proof of concept.

The films that are used to encapsulate the IDA were formed by preparing a solution of 7 mL of $dH_2O$ and 350 mg of pullulan powder (dissolved completely) and cast into a 3.5 cm Falcon petri dish. Then, ½" circular films were punched out of it, and a thick pullulan solution (used as a glue) was added to the films around the outside to stick them together (with the IDA solution/powder in the centre).

The films that were used to encapsulate the enzyme (AChE) were formed by mixing 0.9217 mL of $dH_2O$ with 46.083 mg of pullulan, and adding the required amount of AChE for each film. Three (3) films with 5 µL of AChE and two (2) films with 10 µL of AChE were tested, in order to determine which volume of enzyme results in a better color change.

In order to cast the films with enzyme, to avoid wasting the enzyme, the films were cast into brass or Teflon rings, on a glass petri dish. It was observed that brass rings on a glass dish or Teflon rings on a plastic dish allowed the solution to leak out underneath the ring, ruining results. Teflon rings on a glass surface and brass rings on a plastic surface were therefore used when casting films.

Capsules Cast in a 96 Well Plate

In order to determine if pullulan capsules can be cast into the 96 well plates, which would allow for automated analysis of color intensity in a 96 well plate, it was attempted to cast some films into several wells. When cast into the wells, different concentrations of the pullulan solution were used, ranging from 50 mg/mL to 350 mg/mL pullulan. The resulting capsules were then checked upon drying, and it was found that the PEG-350 ingredient in the solution resulted in holes being formed in the capsules. Nonetheless, each capsule was formed in the correct shape, although the 50 and 100 mg/mL concentration capsules were too thin to be useful. 400 µL of pullulan solution was added to each well.

Enzyme Activity Testing

In order to determine if the casting method reliably worked for immobilizing enzymes within the pullulan solution, the portions of the film that leaked out of the brass rings onto the plastic petri dishes were collected and tested. Three samples were tested:

5 mg/mL AChE, ~10 mg film, 50 µL $dH_2O$, 2 mg IDA→slight greenish blue color change, but not nearly noticeable enough to be satisfactory.

10 mg/mL AChE, ~10 mg film, 350 µL $dH_2O$, 5 mg IDA→too much water present for any detectable color change.

10 mg/mL AChE, ~10 mg film, 50 µL $dH_2O$, 10 mg IDA→slightly greenish color change, no blue. Color changed to yellow overnight for reasons unknown (most likely excess IDA)

The films that were cast with the enzyme (the amount that did not leak from under the brass rings) were tested simultaneously with IDA, but no color change was visible.

It is hypothesized that the lack of enzyme activity was due to either (a) the film being too thin, resulting in poor protection of the enzyme, or (b) while drying, too much of the enzyme came into contact with oxygen due to recirculation within the pullulan solution.

Best Concentrations for Color Change

To determine the ideal concentration (of enzyme and pullulan) that allows for a good color change that will noticeably diminish with pesticide presence, several trials were conducted with different concentrations. Considered were pullulan concentrations of 125 mg/mL and 250 mg/mL and AChE volumes of 5 µL and 10 µL respectively. Four samples were prepared by mixing the pullulan and water together, to form 40 µL, then the enzyme was added and the total volume was set to 50 µL (by the addition of water). 2 mg of IDA was added to each tube.

| Tube | Pullulan (mg/mL) | Water (µL) | AChE (µL) |
|---|---|---|---|
| 1 | 125 | 5 | 5 |
| 2 | 125 | 0 | 10 |
| 3 | 250 | 5 | 5 |
| 4 | 250 | 0 | 10 |

It was observed that in the short term, the color intensities developed in tubes 1 and 2 (lower concentrations of pullulan) were darker, but in long term, the intensities of 1 and 3, and 2 and 4 respectively, matched very closely. This indicates that: (a) the volume of enzyme is directly related to the intensity of color change, ie. the more enzyme is present, the more intense the color change will be, and (b) a higher concentration of pullulan results in the reaction occurring slower, but the end result (intensity) is the same, it just takes longer to reach it.

It may not always be the case that the most intense color change is the most desirable, as it is more difficult for low concentrations of pesticide to diminish the color noticeably, so this could result in some false negative results if the color change is too intense. In order to test if the color change will be approximately the same when the same solutions are dried, four eppendorf tubes were prepared with solutions matching those in tubes 1 and 4 from the previous results.

| Tube ID | Pullulan (mg/mL) | Enzyme (μL) |
|---|---|---|
| 1-1 | 125 | 5 |
| 1-2 | 125 | 5 |
| 4-1 | 250 | 10 |
| 4-2 | 250 | 5 (ran out) |

35 μL of $dH_2O$ was added to tube 1-1, and a distinct blue color change was observed quite quickly (>15 minutes). When left out overnight (eppendorf tube uncapped), the color turned to a dark blue/green, as illustrated in FIG. 6.

Two microcentrifuge tubes were left (1-2 and 4-2) that can be tested at a later time to ensure that the pullulan protects the AChE from oxidation.

IDA in PVA Test (Protection Test)

15 μL of IDA dissolved in methanol was added to a pullulan capsule (cast in an eppendorf tube lid), and sealed with a 5 mL (50 mg/mL, 3.5 cm petri dish) PVA film using a PVA glue solution. Another capsule was prepared with IDA in a powdered form. The capsules were left to determine if the PVA will serve as an oxygen barrier to protect the IDA from oxidation over a period of time Creating New Sensor Devices In order to make a paperless sensor, it is desirable to allow for ~5 minute incubation of the enzyme within the water before the IDA is released. In order to do this, it is theorized that the eppendorf tubes that were previously used can have a thin layer of enzyme cast overtop of a capsule containing IDA in the bottom of the eppendorf tube. This layer of enzyme-containing pullulan should be thick enough to not dissolve through the pullulan capsule, and to allow the solution to dry.

The previously formed capsules that were cast in the smallest eppendorf tube cap lids, and filled with 5 μL of IDA solution were sealed with a 5 mL pullulan film, and the edges of the film cut off. The entire capsule was then placed into tube 4-1 (containing 10 μL of enzyme).

FIG. 7 demonstrates the visible color change of the solution when 35 μL of $dH_2O$ is added.

Capsule Tests with Pesticide and Control

In order to determine if a similar sensor setup will work (AChE and IDA), and to see if a new standard curve will need to be generated, several tests were performed.

5 μL of AChE was added to 40 μL of 250 mg/mL pullulan solution, and cast into a 0.6 mL Eppendorf microcentrifuge tube. A 2 mm (diam)×4 mm (depth) capsule with an enlarged flange was filled with 5 μL of IDA (cap thickness of 5 mL, diam of 5/32"), and added to the Eppendorf tube 5 days after casting.

30 μL of $dH_2O$ was added to the tube, to dissolve the capsule and allow for the reaction to occur.

The resulting color intensity increases over time, and turns a blue color, as indicated by FIG. 8. As can be seen, the color intensity change is lessened after 15 minutes, as the reaction nears completion, and slows down.

To ensure that the observed color change is due to the reaction of IDA with AChE, samples are tested with an organophosphate pesticide (concentration of 10-3), and two control samples, as demonstrated in FIG. 9. It is evident that there is a color change for the sample tube with $dH_2O$, as expected, and at time of 15 minutes for the sample containing no enzyme, there is no visible color. However, when the time is extended to 60 minutes, there is a faint bluish color, that may be due to possible contamination, or due to an unknown side reaction of the IDA (perhaps with pullulan).

Masses of Pullulan Capsules

The masses of pullulan capsules cast of 250 mg/mL pullulan solution are measured, and the average value (with standard deviations) are calculated in order to determine how homogenous the samples are. The results are indicated below which gives the average mass and standard deviation for each type of pullulan capsule cast of 250 mg/mL solution.

| Type | Average ± St. Dev. (mg) |
|---|---|
| Small (holes) | 3.80 ± 0.28 |
| Small (no holes) | 4.95 ± 0.79 |
| Medium (holes) | 11.60 ± 2.44 |
| Medium (no holes) | 13.37 ± 3.42 |

The sources of variation in these capsules are due to variations in the capsule mold, and possible differences in the volumes added. It is suggested to add a prescribed volume of solution to each of the capsule molds to ensure the same mass of pullulan results.

Casting IDA into Pullulan

In order to determine if pullulan works to stabilize IDA when the IDA is mixed into the pullulan solution, a solution of 300 mg/mL pullulan was mixed, and 5 μL of IDA dissolved in methanol was added to each 30 μL of sample. A thick pullulan solution was used to minimize the amount of contact with water the IDA will have, to minimize the hydrolysing (hence inactivation) of the IDA.

Five samples were cast (total volume of 35 μL) into the caps of 0.6 mL Eppendorf microcentrifuge tubes and left to dry. The activity of the IDA will be measured by:

i. checking for a pink/red color change, which indicates the IDA is hydrolysed or oxidized ii. testing with AChE to ensure that a blue color change still results Pesticide Tests Three trials were conducted with fresh malathion (from Bioninterfaces Institute), which was diluted with Tris buffer to a concentration of 10-2 mol/L. A control sample was also done with 5 μL of AChE and 250 mg/mL pullulan to ensure that a color change would occur. The color change was initially green (~2 minutes), then became a blue color which increased in intensity over time.

Information about the contents and the results of each Eppendorf tube test with pesticides is presented below. A control test was performed with 5 μL of AChE and 30 μL of $dH_2O$ with 5 μL of IDA/methanol, and the color change to blue-green was very quick.

| No. | AChE (µL) | Pullulan (mg/mL) | Volume (µL) | Incubation Time (min) |
|---|---|---|---|---|
| 1 | 5 | 250 | 30 | 15 |
| 2 | 10 | 125 | 30 | 30 |
| 3 | 5 | — | 40 | 30 |

| No. | Result |
|---|---|
| 1 | solution turned cloudy upon addition of the IDA/methanol. No color change at 5 minutes. |
| 2 | Slow color change to blue (about 5 minutes to be noticeable on camera, 10 to be noticeable by eye), then color intensified to near the color of the control sample. |
| 3 | Sample was accidently further diluted with 5 µL of Tris buffer, and the color change was very slow (similar to 2), and eventually resulted in a dark blue color that was several shades lighter than (2). This may be due to dilution, or perhaps the fact that the AChE was indeed more inhibited. |

Since the AChE acts as a catalyst (not a reagent) in this reaction, it is possible that even if a small fraction of the AChE is not inhibited by the pesticide (regardless of concentration), the small amount of AChE could act to degrade a significant proportion of the IDA, but it would take longer. This could explain the anomalous results obtained thus far. On a paper-based device, the immobilized AChE is limited to degrade the IDA that is immediately around it. However, when in solution, the AChE is able to contact with much more of the IDA and degrade it, but it would take longer.

Reaction Kinetics

In order to know how much of each reagent and enzyme to add to the solution, it is desirable to know more about how the reaction proceeds. The kinetics (and mechanism) of the hydrolysis of N-methylindoxyl acetate is known (M H Sadar, K J Laidler. Transient Kinetics of the Acetylcholinesterase Catalyzed Hydrolysis of N-Methylindoxul Acetate. Can J Biochem. 1974). N-methylindoxyl acetate is structurally quite similar to indoxul acetate, with the exception of a single non-reacting methyl group attached to the nitrogen atom. Due to the structural similarities, then, the kinetics are assumed to be quite similar. The rate law expression of this reaction follows the Michaelis equation as:

$$v = k_c^* [E]^* [A]/(K_M + [A])$$

with $k_c = 320$ s$^{-1}$ and $K_M = 2.58 \times 10^{-3}$ M.

The enzyme and substrate concentrations must be converted to units of mol/L in order to use the rate law equation. Accordingly, for the enzyme it is known that there is a 500 U/mL concentration in solution, and 513 U/mg of the solid powder. Additionally, according to published material (S R Levinson, J C Ellory. The Molecular Form of Acetylcholinesterase as Determined by Irradiation Inactivation. Biochem J. 127. 1973. 123-125) the approximate molecular weight of a single acetylcholinesterase molecule is ~75000 g/mol. Using this information, the concentration of the enzyme can be calculated. The concentration of the IDA in the solution is provided by the prepared IDA solution, then adjusted to account for the increased volume in the Eppendorf tubes.

Trials with Different Concentrations

It was attempted to use different concentrations of the enzyme and IDA in order to optimize the color intensity, while ensuring that the intensity is low enough that there is a noticeable decrease in intensity when pesticides are applied. Accordingly, several Eppendorf sample tubes were prepared as outlined below which gives conditions of the different Eppendorf tubes prepared to test the effects of concentration of enzyme.

| Sample # | [IDA] (mol/L) | [AChE] (mol/L) |
|---|---|---|
| 1-1 | $4.762 \times 10^{-4}$ | $3.064 \times 10^{-10}$ |
| 1-2 | $9.302 \times 10^{-4}$ | $2.993 \times 10^{-10}$ |
| 2-1 | $2.174 \times 10^{-3}$ | $2.798 \times 10^{-10}$ |
| 2-2 | $9.709 \times 10^{-5}$ | $3.124 \times 10^{-10}$ |
| 3-1 | $4.651 \times 10^{-4}$ | $5.986 \times 10^{-10}$ |
| 3-2 | $9.091 \times 10^{-4}$ | $5.850 \times 10^{-10}$ |
| 4-1 | $2.128 \times 10^{-3}$ | $5.477 \times 10^{-10}$ |
| 4-2 | $9.479 \times 10^{-5}$ | $6.100 \times 10^{-10}$ |

The sample sets 1 and 3 were first tested to determine the color change intensity. It was found that the color change began around the 1 minute mark, and continued to increase in intensity until about 30 minutes. At the 15 minute mark, the color intensity was nearly as developed as it would become overnight. A 15 minute test time is suggested.

The results of sets 1 and 3 were that the maximum color intensity was observed for the 1-1 sample. This is unexpected, as it represents the lowest concentrations of both the substrate and the enzyme of all the others.

Upon analysis of the kinetics information, as pictured in FIG. 10, it was determined that according to kinetic theory as previously mentioned, the expected order of intensity is 3-2>3-1>1-2>1-1.

However, the results of the color intensity measurements, as performed by ImageJ as previously described[6], revealed that the expected trend was not followed. Rather, as demonstrated, the color intensity of 1-1 was the darkest, followed by 3-2, 3-1 and 1-2. It is possible that different lighting conditions between the trials may have resulted in some random error for measuring the average color intensity.

Upon further testing, it was discovered that what appears to be the ideal concentration of enzyme and substrate is 1 uL of AChE, 40 uL of 100 mg/mL pullulan solution and 1 uL of IDA. The color change is rapid (~1 minute to begin), and distinctly blue against any background.

Testing IDA Capsules and Pullulan Films

Previously explored was the addition of IDA (solution and powder form) to two PVA capsules. 5 uL of IDA dissolved in methanol was added to one, and IDA in powder form was added to the other. When the samples were tested by the addition of Tris buffer to dissolve the capsule and AChE to measure the activity of IDA, a very distinctive blue color change was observed, indicating that the IDA was kept stable over a period of two weeks (approximately). Additionally, it was noted that the IDA solution was rapidly released, and resulted in a color change quite quickly, while the powdered form required a much longer time and required the addition of more Tris buffer and mixing in order to change color. Over the weekend, the color intensity was approximately the same however, indicating that it is a kinetic problem, not a molecular stability issue.

Also tested was one of the capsules with IDA solution cast into a pullulan film (in the lid of a 0.6 mL eppendorf tube). The same distinct blue color change occurred, indicating that the IDA retained its activity when protected by the pullulan film. Four more capsules were to be left, and tested each week to determine if there is a decrease in the activity of the IDA over a longer time period. For now, it can be stated that the pullulan protects the IDA from hydrolyzation/oxidation for ~2 weeks reliably.

Comparison of AChE Activity w/Different Concentrations of Pullulan

To determine the effect the concentration of pullulan has on the maintenance of the AChE enzyme two samples of 2 weeks age were tested (125 and 250 mg/mL). The resulting color change demonstrated that the activity of the enzyme was not much decreased over a period of two weeks. More trials will be conducted at 1 week intervals to determine if there is a noticeable color intensity difference over time.

Spectrophotometry

As a method of tracking the reaction progress and quantifying the color change due to pesticide inhibition a spectrophotometer was used. The spectrophotometer requires a minimum volume of 700 μL of sample to be placed into a cuvette, which is then individual read. This is time consuming, but provides a quantifiable method of determining the color intensity (and repeatable method).

For the first experiment, 10 different samples, and one blank sample. 1 μL of AChE was cast into the bottom of a 0.6 mL Eppendorf tube, in 200 mg/mL pullulan (40 μL volume). The resulting solution then had pesticide (diluted in Tris buffer) added in the volume of 160 μL. For the blank sample, no IDA was added, while for the other 10 samples, 1 μL of IDA was added (in aqueous form). Pesticide (malathion) was added in various concentrations to quantify the inhibitory effect of the pesticide on the enzyme.

FIG. 11 demonstrates the curve that resulted from this experiment, demonstrating that the higher the concentration of pesticide, the lower the color intensity that results is. This result is expected, but there is some variation about the expected trend. A sigmoid curve is fitted to the data (for the 'inverse s-shaped curve).

Two wavelengths were tested, the theoretical wavelength of the IDA color change (605 nm) and the result of a wider-spectrum scan (725 nm) were tested.

Multiple Well Samples (BI Spectrophotometer)

In order to track the kinetics of the enzyme activity (rather than simply a color change at one point in time), the 96 well plate with spectrophotometer in Biointerfaces Institute was used. This scanner allows for the absorbance of each well to be measured as a function of time (scans~every 9 seconds). A constant amount of AChE (1 μL) was added to each sample. Each sample contained 40 μL of a 150 mg/mL pullulan solution, and is diluted with 159 μL of Tris buffer (where the pesticide will eventually be).

Using the plots of the concentration of IDA (substrate) vs. the absorbance (at 605 nm), the initial rate of the enzyme reaction can be calculated as the $k_m$ value of the enzyme (characteristic). The $k_m$ values can then be plotted onto a curve comparing the $k_m$ as a function of pesticide concentration.

Measurements are taken by Tecan infinite M1000 reader (microplate reader).

Several different methods of solution preparation were used, including:
  i. mixing all the pullulan, Tris and enzyme in an eppendorf tube, then adding to three separate wells and adding IDA simultaneously to each well
  ii. preparing each well independently, and adding the IDA solution simultaneously to three wells
  iii. preparing wells independently, and adding the IDA separately, but keeping track of the timing between each well so as to adjust the plot.

Different patterns of well that were used in the 96-well plate were also explored, as demonstrated in FIG. 12 below.

Method of Data Analysis

The data returned by the 96-well plate reader (both Tecan Infiine M1000 and M200 Pro) was analysed by plotting the absorbance of each sample as a function of time. The time scale was adjusted to set the initial time as the start of reaction, not as the start of measuring (for example, immediately after measuring began, the time reading was 0.00 for every sample. However, the actual time of reaction was up to 3 minutes already).

The initial slopes of the absorbance curves were then obtained via linear regression. Two intervals were considered, from 0-500 s and from 0-1500 s (reaction time, not readout time). These slopes (units of $abs*s^{-1}$) were then plotted as a function of the concentration of IDA added to each well. A concentration range of 0-5 mM was considered (final concentration).

After a certain time period, the absorbance reaches a plateau, as the reaction reaches completion. The speed of the reaction depends on the amount of enzyme that is present. The sensor papers operated with 4-5 uL of AChE (500 U/mL), but this is far too much for a liquid phase reaction, and even pesticide of concentration $10^{-2}$ M was unable to inhibit the enzyme. Accordingly, an enzyme volume of 1 uL of 250 U/mL was chosen, and seems to work well. The time of the reaction to reach completion (plateau) is about 30 minutes, as demonstrated in FIG. 13.

IDA Auto-Hydrolyzation

The plots that were obtained, however, did not account for the auto-hydrolyzing of the IDA. The wells were diluted with Tris buffer, in which IDA will degrade. Accordingly, a blank sample was set up (with no enzyme, but all other reagents similar to the real trials), and the slope of the absorbance vs. time curve was obtained for each IDA concentration. This slope (related to rate of reaction) was then subtracted from the slopes of the trials with enzyme, to ensure that the reaction (and color that resulted) was due to the activity of the enzyme, and not the IDA hydrolysis without the enzyme.

For the concentrated IDA solutions that were prepared in methanol (up to 200 mM), it was observed that the resulting color after a time period was yellow. However, there is a possibility that this color could interfere with the spectrophotometer results. FIG. 14 below demonstrates the slopes of the absorbance vs. time curves for the control samples.

Results of the Well Plate Reader

The results of the well plate reader is a plot of the reaction rates (correlated to $abs*s^{-1}$) as a function of the concentration of IDA solution used. FIG. 15 below demonstrates the final plots, as obtained using Sigma software for both the 0-500 s and the 0-1500 s case.

Pullulan Interference and Protection

Pullulan in the solution is supposed to protect the enzyme from being inactivated over time. Accordingly, a trial was conducted in which a 5-day old enzyme and pullulan solution was redissolved and added to a well, and tested against a fresh pullulan sample (with the same amounts of IDA and AChE).

Additionally, a sample of Tris buffer with no pullulan is tested, to compare the effect the addition of pullulan has on the reaction kinetics. Since the pullulan increases the viscosity of the fluid, it is expected that the result be a slow reaction. FIG. 16 demonstrates the results.

AchE Stability Over Time

In order to quantify the protection that pullulan provides to AChE over time, it was attempted to create a set of samples (40) which will be tested over time. Each sample (cast into a 600 μL eppendorf tube) contains:
  i. 40 μL of 200 mg/mL pullulan solution
  ii. μL of AChE (250 U/L)

Each sample tube was allowed to dry, then was sealed and placed into a plastic bag and stored at ambient conditions (~20° C.). At selected time points, the activity of the solution was tested by measuring absorbance over time, and finding the associated reaction rate (corresponding to the activity of the enzyme). To measure the activity, three (3) samples were taken (to establish triplicate repeats), and 195 μL of Tris buffer (100 mM, pH=8.0) was added to each Eppendorf tube and allowed to dissolve the pullulan/IDA film. The resulting solution was then added to a 96 well plate, and absorbance was measured continuously at 605 nm after the addition of 5 μL of 80 mM IDA. The results of these trials are demonstrated in FIG. 17.

Different Pullulan Concentrations

Trials were also conducted with different pullulan concentrations to determine which pullulan concentration results in the best protection of the enzyme. 40 μL of each pullulan solution was added with 1 μL of AChE (250 U/L) and cast into the lids of a 600 μL Eppendorf tube.

The resulting film/capsule/pill was then used by dissolving it into 195 μL of Tris buffer (100 mM, pH=8.0), and pipetted into a 96 well plate, where 5 μL of IDA (80 mM) was added to the well. The absorbance was measured over time to obtain a resulting reaction rate. The final results are shown in FIG. 18.

Samples were left for 4 days in the refrigerator to be casted, and then tested. Error bars are presented as one standard deviation based on triplicate repeats. 40 μL of pullulan solution (various concentrations) was used, and 5 μL of 80 mM IDA was added to each sample. The resulting data does not show any statistically significant trends, due to exorbitantly high error bars (due to so many source of error and variation in experimental setup). The data does suggest an increase in the rate of reaction which peaks at a pullulan concentration of 100 mg/mL. Therefore at lower pullulan concentrations, the film formed is too thin to protect meaningful amounts of enzyme, while at higher concentrations, the increased solution viscosity hinders diffusion and mixing properties, as well as extends the drying time of the capsule (increasing risk of enzyme degradation by oxygen/heat/etc).

Ellman Assay in Solution & on Paper

While indoxyl acetate (IDA) does provide a good substrate to measure the activity of AChE, the Ellman assay (using ATCh and DTNB as substrates) is much more widely used in enzyme research. Accordingly, the necessary reagents were obtained, and preliminary testing began.

When tested in solution, with the following amounts of reagents were used:
  i. 15 uL ATCh (300 uM), 1 uL AChE (10 or 250 U/L)
  ii. 50 uL of 500 uM DTNB
  iii. 34 uL Tris It was noted that the color change (yellow) in solution remained for some time before fading. However, when a paper strip was dipped into the solution and allowed to dry, the color faded overnight. This may be partially due to the reaction products being unstable on a paper substrate, as well as difficulty identifying a light yellow color change on a white background.

Acetylthiocholine (ATCh) is an unstable molecule, and will hopefully be stabilized on paper. However, after several tests were performed, it was noted that after being left in the refrigerator for several days, and left in a fume hood with no protection against hydrolyzation, the ATCh was still stable when tested. The most likely reason for the continued activity of the ATCh is due to the Tris buffer it was dissolved in being evaporated, and the ATCh in a solid (or powdered) form is stable. Accordingly, it should be reliable to store the ATCh as a powder form, preferably inside of a soluble (pullulan) capsule.

Example 3: Further AChE/IDA Bioassays

Materials

Acetylcholinesterase (AChE, from *Electrophorus electricus*, EC 3.1.1.7), and indoxyl acetate (IDA) were obtained from Sigma-Aldrich. Pullulan (MW ~200000) was purchased from Polysciences, Inc and malathion was obtained from Fluka. Human serum albumin (HSA; fatty acid and globulin free, ≥99%) was obtained from Sigma-Aldrich (Oakville, ON). Quartz microscope slides were purchased from Chemglass (Vineland, N.J.) and cut to approximate dimensions of 8×32 mm. Water was purified with a Milli-Q Synthesis A10 water purification system. Buffer salt (Tris 100 mM) and pullulan solutions were filtered using a Pall® syringe filter with 5 μm membrane in order to remove any dust particulate.

Experimental Procedures

IDA Tablets, Creation and Activity Test.

To test the ability of pullulan to retain IDA activity, 10 μL of 40 mM IDA and 40 μL of 120 g/L pullulan in water were mixed and casted in a polypropylene mold with wells with a size of 3 mm in diameter×3 mm in depth. The solution was air-dried overnight at 21° C. and 48% RH; tablet formation was considered not fully completed if the tablet could not be removed from the bottom of the well. The resulting tablets were kept at room temperature for different lengths of time before being tested. To test IDA activity, 199 μL of Tris-HCl (100 mM, pH 8) was used to dissolve the pill and 1 μL of fresh 250 U/mL AChE was added. The solution was then transferred to a 96-well plate and the absorbance of the developing blue color was measured at $A_{605}$ on a TECAN Infinite M200 Pro microtiter plate reader.

AChE Tablets, Creation and Activity Test.

To test the ability of pullulan to retain AChE activity, 1 μL of 250 U/mL AChE and 40 μL of 120 g/L pullulan were mixed and casted into tablets. The solution was air-dried overnight at 21° C. and 48% RH; tablet formation was considered not fully completed if the tablet could not be removed from the bottom of the well; and the resulting tablets were kept at room temperature for different lengths of time before being tested. To test AChE activity, 195 μL of Tris-HCl (100 mM, pH 8) was used to dissolve the tablet and 5 μL of fresh 80 mM IDA was added. The solution was then transferred to a 96-well plate and the absorbance was measured at $A_{605}$ on TECAN Infinite M200 Pro microtiter plate reader.

Malathion Detection Test.

200 μL of malathion solution was added into the Eppendorf tube followed by the addition of the pullulan-AChE tablet. After 5 minutes of incubation, the pullulan-IDA tablet was added into the Eppendorf tube. The mixture was incubated for 10~15 minutes for development of the blue color; the concentration of malathion was calculated based on the color intensity. Images were obtained using a Galaxy Nexus cellphone camera operated in automatic mode with no flash.

The Images were analyzed using ImageJ software by methods described elsewhere[6]. The concentration range of malathion was 0.01 to 1E-10 M.

Preparation of Pullulan-HSA Solutions and Films.

Human serum albumin (60 µM final concentration) was dissolved into either 100 mM Tris-HCl (pH 7.5) or 100 mM Tris-HCl containing 10% pullulan. These pullulan solutions, with or without HSA, were carefully pipetted onto the quartz slides (500 µL/slide) and allowed to dry overnight at 21° C. and 48% RH in order to produce the film samples.

Determination of the Water Content in Pullulan Films.

The water content of films was done by gravimetric analysys with drying at 130° C. until constant weight. The water content in the films was found to be 0%.

Fluorescence Intensity Measurements.

Fluorescence measurements were acquired using a Cary Eclipse fluorescence spectrophotometer. Solution samples were measured in quartz cuvettes and continuously stirred throughout the experiments. Film samples were suspended in quartz cuvettes at a 45° angle to the excitation light using specialized holders which reflected excitation light away from the detector and collected emission through the slide and into the monochromator/PMT.

For fluorescence emission spectra, samples were excited at 295 nm (to ensure that the light was absorbed almost entirely by the lone tryptophanyl residue) and emission was collected at 310-450 nm in 1 nm increments, using a 5-nm bandpass for both excitation and emission paths and an integration time of 0.1 s. Spectra from both solution and film-based samples were corrected for light scattering by blank subtraction of signals originating from buffer or pullulan/quartz materials, respectively, without HSA. All the spectra were also corrected for deviations in emission monochromator throughput and PMT response and smoothed by the Savitzky-Golay method, using a factor of 5 and an interpolated factor of 5.

For thermal denaturation studies, the temperature was raised in ~5° C. increments from 20° C. to 90° C. and allowed to equilibrate at each temperature for at least 5 min. The temperature in the cuvette was measured directly with a thermistor probe. Intensity-based unfolding curves are reported as integrated scan intensities, which are normalized to the integrated intensity at the beginning of the experiment (20° C. as 100%) for each sample. Emission scans are measured in relative fluorescence units, RFU, and all values are reported as the average of three separate samples.

FIG. 19 shows a graph of the reaction rate (abs/s) of AChE and IDA as a function of the IDA concentration from 0 to 4 mM. The reaction rate of AChE tablet with different concentration of IDA was monitored to establish an optimal IDA concentration for pesticide detection experiment. From the data, the concentration of IDA for the pesticide was chosen to be 2 mM (which is significantly larger than KM). The error bars represent the standard deviations based on triplicate repeats.

FIG. 20 shows the fluorescence intensity-based thermal unfolding curves for HSA-buffer solution, in HSA-pullulan solution and HSA-pullulan film. Changes in the intrinsic fluorescence from tryptophan (Trp) residues within proteins can be used to provide information on protein conformational stability and unfolding[7]. Therefore, steady-state fluorescence spectra were measured at various temperatures for HSA-buffer solution, HSA-pullulan solution and HSA-pullulan film (HSA was chosen for this study because it contains a single Trp allowing for unambiguous investigation[8]. The data shows that the intensity of fluorescence for HSA-buffer and HSA-pullulan solution decreased by more than 90% when the temperature was raised from 20° C. to 90° C., while that of HSA-pullulan film only decreased by ~70%. The unfolding temperature (wherein the Trp intensity is reduced by 50%) was significantly higher for the pullulan-HSA film at ~80° C., versus ~60° C. for both HSA-buffer and HSA-pullulan solutions. This study demonstrates that pullulan film significantly enhances the thermal stability by preventing substantial unfolding as a result of molecular confinement in the rigid matrix. This stabilizing effect is only observed in the pullulan film and not in the pullulan solution.

Discussion

Individual AChE-pullulan tablets and IDA-pullulan tablets were produced by using a process that involves 1) the mixing of a pullulan solution with either an AChE or IDA solution, 2) the casting of each mixture into a polypropylene mold with small wells (3 mm in diameter_3 mm in depth), and 3) air-drying. Note that defined concentrations of AChE and IDA were chosen to achieve a maximum rate of color formation (see FIG. 19). To conduct the assay, an AChE tablet was added to the sample to allow preincubation with the pesticide followed by the addition of an IDA tablet. If malathion is present, the sample remains colorless or turns faint blue (dependent on the concentration of malathion, as discussed below). In the absence of malathion, IDA is fully hydrolyzed by AChE and the test sample turns deep blue.

The tablet system can not only be used achieve qualitative colorimetric detection of malathion by eye, it can also provide quantitative analysis of the pesticide concentration in a test sample when using a smartphone and image-processing software (such as ImageJ[6]). FIG. 21 shows a plot of the dose-dependent inhibition of AChE by malathion, with data obtained using a smartphone. This simple method can be used to detect malathion at levels as low as 64 nm (S/N=3).

The long-term stability of both the AChE and IDA tablets was tested. As shown in FIG. 22, AChE stored in solution at room temperature became completely inactive within 3 days. Similarly, IDA in solution at room temperature lost 70% of its activity within one day and become completely inactive within a week. In sharp contrast, both AChE and IDA in tablet form remained fully active for at least 2 months when stored at room temperature. In the case of IDA, the loss in performance was related to oxidation.[16] Data suggests that pullulan acts as a strong barrier to oxygen, an effect that is consistent with previous findings.[7,9] In theory, an antioxidant could be used to prevent the oxidation of IDA during storage at room temperature. However, the antioxidant would also inhibit the formation of indigo during the assay.

The loss of AChE activity, however, is attributed to thermal denaturation. To further examine the role of pullulan in stabilizing AChE, activity of AChE was monitored as a function of temperature. For this experiment, native (unencapsulated) AChE and the corresponding pullulan tablet were treated at a given temperature for 30 min, followed by activity assessment at room temperature. FIG. 23 shows that the free AChE became completely inactive following a 30-minute heat treatment at 50° C. or above. In stark contrast, AChE tablets retained ca. 90% of their initial activity even after a 30-minute incubation at 90° C. Significant thermal stabilization was also observed for human serum albumin (FIG. 20) where the unfolding temperature of the protein, as determined by tryptophan emission intensity, increased by 20° C., thus demonstrating that the stabilizing effects of pullulan are generic.

Example 4: Highly Stable 'All-in-One' Bioluminescent Pill for Sensitive ATP Detection Materials.

Luciferase, Luciferin, Co-enzyme A (CoA), Adenosine triphosphate (ATP), Tricine, Magnesium Carbonate ($MgCO_3$), Magnesium Sulfate ($MgSO_4$), DL-Dithiothreitol (DTT), Ethylenediaminetetraacetic acid (EDTA), and Dextran (Mw~148000) were purchased from Sigma-Aldrich. Polyethylene glycol (PEG, Mw~6000) was purchased from Fluka. Pullulan (Mw~200'000 Da) was purchased from Polysciences.

Preparation of 'All-in-One' Pullulan Pill.

All reagents for the luciferase assay except for adenosine triphospate (ATP) were casted in a single pullulan pill. For the pullulan pills aqueous solutions of 10 mM Luciferin, 100 mM Luciferase, 27 mM Coenzyme A (CoA), 170 mM Dithiothreitol (DTT), 10 mM Ethylenediaminetetraacetic acid (EDTA), 107 mM $MgCO_3$, and 267 mM $MgSO_4$ were prepared. 200 µL of each solution was added to 8 mL of 12 w/v % Pullulan solution. Lastly, for each pill 47 µL of the final solution was pipetted onto a PET film and dried in a glove box under nitrogen. The casted pills were then stored at room temperature.

Buffer Preparation.

A buffer solution containing ATP was prepared to test the activity of the luciferase pills. For the buffer solution, 16 mL of water was added to 2 mL of 2.5 mM ATP and 2 mL of 200 mM Tricine and the pH was adjusted to pH 7.8.

Stability at Room Storage Condition.

Once the pills were completely dried, they were collected in dark bottles. The pills were stored at room temperature and the activity of the pills was tested over time. On the day the pills were prepared, the activity of the fresh pullulan and reagent solution was tested. 47 µL of the solution and 100 µL of the buffer were added to a 96 well-plate and the luminescence was measured using the TECAN M1000. On subsequent days, the activity of the pills was measured by placing a single pill into a well and 100 µL of ATP buffer. Each test was performed with three repeats.

ATP Detection Assay.

The sensitivity of the luciferase assay was also investigated. To determine the detection limit of the assay, different ATP buffers were prepared with concentration ranging from 0 µM to 1000 µM and tested it with luminescent pills.

Thermal Stability.

Reagents in solution and pullulan pills were incubated at each temperature set point for 30 minutes in a hot plate. After that, they were allowed to cool until room temperature was reached. Then the luminescence reading was taken using 100 uL of 250 uM ATP (in tricine buffer)

Stability in Dextran/PEG.

The effect of other polymers and polysaccharides on luciferase activity was investigated. Dextran and PEG pills were prepared using the same procedure as the pullulan pills. In place of pullulan solution, 12 w/v % Dextran and 12 w/v % PEG solutions were used to create dextran and PEG pills respectively.

For comparison, the same study was repeated with dextran and polyethyleneglycol as additives. (PEG and Dextran cannot be used as stabilizer as they do not preserve the luciferase, data not shown).

Cell Assay Using Luminescent Pill:

E. coli DH5α cell cultures were started from a glycerol stock and grown in Müller Hinton (MN) media at 37° C., 250 rpm, for 18 hours. A 1:50 dilution of the overnight culture in MH broth was created and grown until log phase ($OD_{600}$=0.3). At this point, a 10 µL of the culture was serially diluted by $10^5$ in sterile PBS and plated, in triplicate, on LB agar plates for enumeration. Cell lysis was performed right before the luminescence testing by adding B-Per in the volume ratio of 1:10 (B-Per: Cell culture) and was incubated for 15 minutes. 100 uL of the lysed cells was added into the well containing luminescent pill.

LC-MS Analysis:

LC Method:

Phenomenex C18 column 100×3 mm dimensions with 3 um particle size was used as stationary phase. 10 mM Ammonium acetate was used as mobile phase with acetonitrile. 14 minutes gradient with acetonitrile goes upto 80% in 10 minutes. Chromatogram was monitored in 254 nm wavelength with UV detector during method development.

Sample preparartion was done by dissolving luciferin pill with 50 uL of water followed by 500 uL of methanol. The precipitated pullulan was filtered using 0.2 um syringe filter.

Ms Condition:

Ionization:

ESI negative mode, Capillary Voltage 400 V with Quadruple analyzer.

Discussion

In this work, pullulan, a polysaccharide comprising maltotriose units was used to form 'all-in-one' luminescent pill for ATP detection. All the components such as luciferase, luciferin, $MgSO_4$, $MgCO_3$, dithiothreitol, ethyl enediaminetetraacetic acid (EDTA), CoA enzyme and tricine buffer, for the luminescence detection of ATP were taken in pullulan (12% w/v final concentration) and encapsulated to form a stable 'ready-to-use' pill. Encapsulation with pullulan not only protects the components because of its oxygen barrier property and polymer crowding but also forms a stable, non-hygroscopic and size/shape-tunable pills after drying. When the luminescent pill was treated with ATP in solution, it readily dissolves and releases all the components for luminescence detection (FIG. 24).

In the present work, the pill-making process involves simple mixing the components and drying in an inert atmosphere to give the luminescent pills. Unlike other polymers used previously for this purpose, pullulan has an additional oxygen barrier effect to it. To the best of the inventor's knowledge, this is the first report in which all the components required for luciferase/luciferin assay were stabilized together as a single 'drop and detect' pill for the ATP detection. The concentration of pullulan for casting the pills was optimized based on two factors viz., retention of glow kinetics and minimum drying time. The glow kinetics was retained between 0.001 mg/mL and 10 mg/mL of pullulan concentration and started decreasing when it the concentration was increased to 100 mg/mL in solution. Also, low concentration. such as 0.001 mg/mL, will have a longer drying time which affects the stability of the encapsulated enzyme. The stability of the pills at room temperature was evaluated by storing the pills at bench top in dark containers. FIG. 25A shows the glow kinetics (luminescent units versus time) of a luminescent pill with 250 uM ATP concentration on a 96 well plate reader (Tecan M1000). FIG. 25B shows the stability of pills in comparison with the same components stored in buffer. This shows that the enzyme loses its activity in buffer solution in few hours. On the other hand, the enzyme and other components in pullulan pills were found to be stable for 3 weeks at bench top. The most unstable components in the pill are enzyme (luciferase) and luciferin. The stability of enzyme alone was also tested in pullulan pills and was found to be active even after four months when stored at room temperature, which led to the study of the luciferin-pullulan pill by a suitable technique, which in this case is LC-MS.

Luciferin, as a substrate for this oxidative-decarboxylation reaction is also unstable at room temperature and prone to auto-oxidation and photo-degradation. One of the potential inhibitors of luciferase is the dehydroluciferin which forms when luciferin is exposed to air. To confirm the exact degradant responsible for the decrease in activity, luciferin alone was casted as pills with pullulan. Four weeks old luciferin pill was taken for LC-MS analysis. When luciferin was extracted with methanol by dissolving the pills with a small amount of water and then with methanol. Pullulan precipitated because of its poor solubility in methanol. Then the suspension was filtered using 0.2 uM syringe filters. The filtrate was expected to have luciferin and its degradant because of its high solubility in methanol. The challenging part was the impurities associated with pullulan were also present in the filtrate as commercial pullulan is not 100%, resulting in too many peaks. Hence, it was decided to use extracted ion chromatogram (EIC) for the key impurities by its m/z ratios. In ESI-MS, pure luciferin in methanol shows up as a single peak at 4 minutes which correlates to two mass peaks, luciferin 279 Da and its decarboxylated product at 235 Da (fragment under ESI condition) in negative mode. Fresh and four weeks old luciferin pills were first analyzed for the above peaks which confirmed its presence. Then, they were analyzed for m/z 277 (dehydroluciferin) and 233 (decarboxylated form). The extracted ion chromatogram (EIC) clearly shows the 233 peak in the four weeks old pill at retention time 5.8 min which was absent in fresh. This confirms that luciferin is converted into dehydroluciferin and/or its decarboxylated form after three weeks which could be a strong reason for the decrease in stability of the luminescent pills after 3 weeks. However, by drying and packing the pills in inert conditions, such as inside dry-box, this problem will be overcome and shelf-life increased.

As these pills encapsulate all the required components, they are highly advantageous as they allow the circumvention of laborious preparations each time of us. It was observed that polymers such as dextran and polyethylene glycol were not able to retain the activity that pullulan provided when they were prepared and tested similarly, which shows pullulan has unique stabilizing effect when compared to other polyols.

The thermal stability of luciferase is known to be very low. The luminescent 'all-in-one' pills were also tested for thermal stability by incubating the pills at temperatures up to 70° C. The activity of the pills remains the same up to 70° C. while in solution it decreases even at 30° C. and lost all its activity at 50° C. This clearly shows that the pullulan protection for luciferase also ensures the retention of activity at elevated temperatures. The ability of luminescent pills for ATP detection was shown in FIG. 26. A series of concentrations of ATP in tricine buffer were added to the pills and the luminescence intensity was measured in a plate reader. The relative luminescent units (RLU) were plotted for the range of concentration. The limit of detection of ATP concentration was calculated to be 16 pM at 3σ above background which correspond to 1.6 fmole ATP in 100 uL which was added to the pill. This value is relatively better in comparison with the recently reported methods[9]. Also, the ability of this pill to detect the lysed *E.Coli* cells was tested and compared with the intact cells (FIG. 27). The detection limit was found to be 1800 CFU for the lysed cells which is comparable to other methods which do not involve amplification or enrichment steps[10]. None of the previously reported methods were as straight-forward and user-friendly as that reported here.

Example 5: Automating Multi-Step Spot Tests Using Integrated Layering of Reagents Materials Acetaldehyde, Sodium nitroprusside, Sodium carbonate, TSB (Tryptic Soy Broth), poly-arginine (MW>70 kDa), CPRG (chlorophenol Red-β-D-galactopyranoside, and Allura Red were received from Sigma-Aldrich. Pullulan (PI20, molecular mass of 200 kDa) was obtained from Hayashibara Co, Ltd, Okayama, Japan. Hydrophobic spray (Heavy-Duty Water Proofer, SOFSOLE, available at sport accessories stores). PET films (Polyester 50 Film, 0.004" thick, clear, Part #8567k44) were purchased from McMaster-CARR (Hamilton, ON, Canada).

pH Adapter

A pH adapter was constructed to demonstrate the sequential release of pullulan films on a paper-based device. The pullulan films were prepared by casting pullulan solution on a PET sheet. Strips of 0.5 cm×2 cm tape were placed onto the PET sheet and the PET sheet was treated with a hydrophobic spray. The strips of tape were then removed, thus leaving hydrophilic areas on the PET sheet for casting the pullulan films. In order to create pullulan films with different pH, several 12% pullulan solutions were prepared with pH ranging from 2-12. HCl and NaOH were used to adjust the solution to the desired pH. 150 µL of the pullulan solution was then added to the hydrophilic area using a pipette. The solution was then air dried to form a film, (see FIG. 28).

The pullulan films were then layered together with films at different pH. Given the self-sealing property of pullulan, 1 µL of 20% pullulan solution was placed on each corner of the film in order to secure the pullulan films onto each other. In the same way, the stack of pullulan films was placed onto a pH indicator paper.

To run the test, the solution was passed through the paper, and the change in pH was observed by the colorimetric changes of the pH indicator paper. The time of the pH change can be delayed or regulated by simply adding neutral pullulan films.

Sensor for the Detection of *E. Coli*.

The sensor comprises two parts: a B-PER pullulan disc and a CPRG paper.

The CPRG Paper.

2 wt % poly-arginine (MW>70 kDa) and 9 mM CPRG (chlorophenol Red-β-D-galactopyranoside) dissolved in water were sequentially printed onto the Whatman #1 filter paper using Canon thermal inkjet printer with the "high print quality" setting.

The B-PER Pullulan Disc.

B-PER lyses any bacterial cells in the sample solution and in the presence of β-galactosidase, CPRG will be hydrolyzed to produce a red-colored product. The B-PER buffer solution was prepared by adding 2 µL of lysozyme and 2 µL of DNase to 1 mL of B-PER reagent. Each B-PER pullulan disc was then created by casting 40 µL of 50:50 (V/V) mixture of 10% pulllulan/B-PER buffer solution on surface of flexible PET sheets and air dried. The CPRG paper, which was prepared by printing CPRG onto Whatman paper, was cut to match the size of the B-PER disc. The B-PER disc was then attached to the CPRG paper using 1 µL of 20% pullulan (works as a glue).

To run the test, the sensor can be placed into a container such as a 96-well plate or a 1.5 mL Eppendorf tube cap. Once inside the container, 200 μL of sample solution was added onto the sensor (assay kit) and incubated for 40 minutes. The sensor turns a red/purple color in the presence of *E. Coli* and a light yellow color in the absence of *E. Coli*. The air dried test papers were then imaged using a handheld scanner (Flip Pal 100C Mobile scanner). The color intensity of the sensing zone was quantified using ImageJ software as described elsewhere[6].

*E. coli* Culture.

*E. coli* (ATCC 25922) was cultured overnight in TSB (Tryptic Soy Broth) media for about 20 hrs at 37° C. with a shaking rate of 200 rpm. (The 5 ml culture was started with one colony picked from an agar plate. No antibiotic.)

Sensor for the Detection of Secondary Amine

Acetaldehyde Pullulan Film.

0.5 g of pullulan was dissolved in 5 mL of water. 1 mL of acetaldehyde was added and mixed using a vortex. It was casted as thin films on the bench top by pipetting out 10 uL drops on PET sheets.

Sodium Nitroprusside-Sodium Carbonate Pullulan Film.

0.1 g each of sodium nitroprusside and sodium carbonate were dissolved in 5 mL water. 0.25 g of pullulan was added and mixed using a vortex. 1 mL of acetaldehyde was added and mixed using a vortex. It was casted as thin films on bench top by pipetting out 10 uL drops on PET sheets.

For both lateral flow paper sensor and z-direction flow sensors, the films were stacked in such a way that the analyte will react with acetaldehyde first followed by SNP and sodium carbonate.

Pullulan Kinetics—Absorbance Measurement

The pullulan films were made by mixing 1 mL of 20 g/L dye (Allura Red or Tartrazine) solution with 12 mL of pullulan solution. 2 mL, 4 mL, and 6 mL of the mixed solutions were then cast onto three different petri dishes to create films with varying thicknesses. The solution in the petri dishes was air dried. Once dried, the films were removed from the dishes and weighed. Films were then hole-punched to produce 1 cm×0.5 cm cut-outs. These cut-outs were weighed and the mass of dye in the cut outs was calculated. A single pullulan film cut-out was added to a 10 mL vial of DI water. From this, 150 μL samples were taken every 15 seconds and placed in Eppendorf tubes. 100 μL of the sample was then added to a 96-well dish. The first sample was taken at time zero, before the film was placed into water. These samples were used to determine the absorbance of the solution at each time to characterize the dye release kinetics. FIG. 29 shows the total mass of Allura Red released from the pullulan film as a function of time for different film thicknesses Furthermore, as depicted in FIG. 30, a similar kinetic study was done for CMC (Sodium carboxy methyl cellulose, MW 250,000), MC (Methyl cellulose), PVA (Polyvinvyl amine, MW 125,000, 87-89% hydrolysis), and HEC (Hydroxylethyl Cellulose). This demonstrates that, depending on the application, different polymers may be combined with pullulan films to prolong the releasing process.

Discussion

Simon's Test

The Simon's test is one of the most widely used methods to detect controlled substances such as methamphetamine, and other amphetamines. The test uses acetaldehyde to react with secondary amines to form an initial enamine product, followed by sodium nitroprusside and sodium carbonate to produce an immonium ion, which subsequently hydrolyzes to give the blue-colored Simon-Awe complex. This test is typically performed through the addition of individual reagents to the test substance in the sequence described above, leading to a color change in the case of a positive sample.

The selection of pullulan concentration for each reagent-pill was based on the right balance between the stabilization effect and the release of the reagents. Higher concentrations (>12%) lead to the formation of thicker pills which will take relatively longer time to dissolve and release the reagents. Also, the stabilization of reagents, especially acetaldehyde at low concentration (<5%) of pullulan was not optimal, therefore, acetaldehyde pills were prepared from 10% pullulan solution and the SNP/sodium carbonate pills were prepared from 5% pullulan solution. To produce the multi-step assay, two issues were investigated. First, the initial reaction involves a volatile reagent, acetaldehyde, which normally would not be amenable to immobilization onto a sensor. Second, pre-mixing of the reactants was to be avoided before addition of test substance. and sufficient time for each step to occur prior to the introduction of the secondary reagents was needed as an incomplete initial reactions would lead to a decreased signal. The above concerns were addressed by trapping the reagents in a solid pill using pullulan, which stabilizes the reagents and also keeps them unreacted with each other, when those pills are stacked.

FIG. 28 shows the reaction sequence for the Simon's test. (FIG. 28*a*), along with results obtained using a conventional lateral flow assay (FIG. 31*b*) and the z-directional multi-step spot test (FIG. 31*c*). The assays were performed using diethylamine (DEA) as a surrogate for methamphetamine to avoid the need to handle controlled substances. For the lateral flow test, acetaldehyde and sodium nitroprusside (SNP) were entrapped in separate pullulan films that were placed sequentially along a paper channel in the x-direction (FIG. 31*b*). When the analyte solution (DEA in water) was wicked through this channel, the reaction steps occurred in the expected sequence and produced a blue-colored product. However, the product spread over a significant area of the paper, and thus the color intensity was decreased. When the same assay was performed using the z-directional spot test, a far more intense color was formed that was retained in a small area owing to the use of a hydrophobic barrier to contain the aqueous sample. The incorporation of the Simons test into this format allows for a simplified, reliable and repeatable method of testing for methamphetamines, requiring minimal resources and personnel training. Further, the required reaction and color development time of ~10 seconds for the spot test format which means that this format is comparable to the liquid phase tests typically carried out for Simon's test.

As shown in FIG. 32, the sensitivity and detection limit for the z-directional test is also superior to that of the lateral flow test when each sensor is challenged with a series of DEA solutions of varying concentration. For the z-directional assay the detection range is between 100 ug/mL to 50 mg/mL, while for the lateral flow test the range is 1 mg/mL to 10 mg/mL. Another benefit of the z-directional assay was the ability to use extremely small volumes of test samples (20 uL) to perform the assay, instead of volumes of ca. 200 uL for the lateral flow test, which minimizes sample dilution and improves detection limits. Finally, the z-direction test required only 10 seconds to perform, while the lateral flow test required ~11 minutes, improving assay time.

*E. Coli* Assay

As a second example that highlights the potential for on-sensor sample preparation, the capability of the z-directional paper-based sensor to initially lyse bacterial cells to release an internal enzyme (β-galactosidase) followed by colorimetric detection of the released enzyme using the chromogenic substrate chlorophenol red β-galactopyranoside, was examined by adapting a previously reported multi-step assay[5] to the automated sequential assay format. The sensor comprises B-PER, lysozyme and DNase cast into a pullulan film that is positioned on top of CPRG treated paper. The resultant paper-based sensor can detect the presence of E-Coli by simply applying the sample solution onto the sensor in a one-step process.

FIG. 33 shows the formatting of the E. coli detection assay in the z-direction that allows sample preparation (cell lysis) and reporting without user intervention. FIG. 33A shows top view of the basic components of the z-directional test, which comprises a pullulan film loaded with a detergent (B-PER), lysozyme and DNase I for cell lysis and enzyme extraction and a paper disk containing CPRG (the substrate for β-galactosidase) and a poly-arginine underlayer to enhance the colorimetric signal. FIG. 30B shows the side-view of the sensor, with the composition of the films and reagents. FIG. 33C shows color intensity results obtained from the assay as a function of bacterial counts, while FIG. 33D shows alternative assay formats for E. coli detection using paper disks, Eppendorf tube caps or 96-well plates, demonstrating the versatility of the z-directional assay approach.

As shown in FIG. 33C, the fecal coliform test can be run simply by introducing the water sample to the assay kit followed by 40 min incubation. The sensor will turn a red/purple color in the presence of E. coli and a light yellow color in the absence of E. coli. To achieve quantitative colorimetric detection of E. coli smartphone camera or mobile scanner and image-processing software (such as ImageJ[6]) can be used. FIG. 33C shows a plot of the color intensity versus concentration of E. coli. This simple, equipment free method can be used to detect E. coli at levels as low as $5 \times 10^5$ cfu/ml.

Example 6: PCR with TAQ DNA Polymerase from Pullulan Pill

Materials.
Pullulan (MW ~200000) was purchased from Polysciences, Inc. Water was purified with a Milli-Q Synthesis A10 water purification system. Buffer salt (Tris 100 mM) and pullulan solutions were filtered using a Pall® syringe filter with 5 μm membrane in order to remove any dust particulate. DNA oligonucleotides were purchased from Integrated DNA Technologies (IDT) and purified by 10% denaturing polyacrylamide gel electrophoresis (dPAGE) before use. Agarose was obtained from Bioshop (Burlington, Canada). The fluorescent images of gels were obtained using Typhoon 9200 variable mode imager (GE healthcare) and analyzed using ImageQuant software (Molecular Dynamics). Taq DNA polymerase (TaqDP) was acquired from Biotools.

```
Forward Primer:
5'-CAGGT CCATC GAGTG GTAGG A

Reverse primer:
5'-GTACG TTCAG GAGCA GTGCG A

Template:
5'-CAGGT CCATC GAGTG GTAGG AGGAG GTATT TAGTG CCAAG

CCATC TCAAA CGACGTCTGA GTCGC ACTGC TCCTG AACGT AC-
this is for PCR.
```

PCR.
The DNA was amplified by PCR. Each reaction mixture (50 μL) contained Taq polymerase (1.5 U), forward and reverse primer (1 μM each), dNTPs (0.2 mM each of dATP, dCTP, dGTP and dTTP), and template (10 nM). In order to produce the Taq-pullulan tablet samples, the Taq polymerase was dissolved into 20 μL of Milli-Q water containing 10% pullulan and allowed to air-dry overnight at 21° C. and 48% RH. DNA amplification was performed by using the following conditions: 30 s at 94° C., 45 s at 50° C., 40 s at 72° C., 18 cycles. PCR product was analyzed by 3% agarose gel electrophoresis.

FIG. 34 shows agarose gel results of PCR products in the presence of different pullulan concentrations. The effect of pullulan concentration on the activity of TaqDP was studied in this experiment. 20 μL of pullulan solution (50, 100, 150, 200 mg/mL) and 1 μL of TaqDP were casted into Eppendorf tubes. The activity of TaqDP was tested after one week. The results show that higher concentrations of pullulan up to ~10-12% provide better protection of TaqDP. Inefficient protection in higher concentrations of pullulan (≥20%) is due to high solution viscosity which causes greater error in the experiments and loosing samples during pipetting.

While the present application has been described with reference to examples, it is to be understood that the scope of the claims should not be limited by the embodiments set forth in the examples, but should be given the broadest interpretation consistent with the description as a whole.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

FULL CITATIONS FOR DOCUMENTS REFERENCED IN THE APPLICATION

[1] a) M. Shibata, M. Asahina, N. Teramoto, R. Yosomiya, Polymer 2001, 42, 59-64; b) R. S. Singh, G. K. Saini, J. F. Kennedy, Carbohydr. Polym. 2008, 73, 515-531; c) A. Imeson, Food Stabilisers, Thickeners and Gelling Agents, Wiley, Hoboken, 2011, pp. 267-274.

[2] S. Farris, L. Introzzi, J. M. Fuentes-Alventosa, N. Santo, R. Rocca, L. Piergiovanni, J. Agric. Food Chem. 2012, 60, 782-790.

[3] A. A. Krumnow, I. B. Sorokulova, E. Olsen, L. Globa, J. M. Barbaree, V. J. Vodyanoy, J. Microbiol. Methods 2009, 78, 189-194.

[4] S. Wu, J. Chen, Int. J. Biol. Macromol. 2013, 55, 254-257.

[5] a) M. S. Hargrove, S. Krzywda, A. J. Wilkinson, Y. Dou, M. Ikeda-Saito, J. S. Olson, Biochemistry 1994, 33, 11767-11775; b) M. R. Eftink, Biophysical Journal 1994, 66, 482-501.

[6] S. Jahanshahi-Anbuhi, P. Chavan, C. Sicard, V. Leung, S. M. Z. Hossain, R. Pelton, J. D. Brennan, C. D. M. Filipe, Lab Chip 2012, 12, 5079-5085; S. M. Z. Hossain, R. E. Luckham, A.-M. Smith, J. M. Lebert, L. M. Davies, R. H. Pelton, C. D. M. Filipe, J. D. Brennan, Anal. Chem. 2009, 81, 5474-5483

[7] a) M. S. Hargrove, S. Krzywda, A. J. Wilkinson, Y. Dou, M. Ikeda-Saito, J. S. Olson, Biochemistry 1994, 33, 11767-11775; b) M. R. Eftink, Biophysical Journal 1994, 66, 482-501

[8] a) D. C. Carter, J. X. Ho, *Adv Protein Chem* 1994, 45, 153-203; b) G. Pico, *Biochem Mol Biol Int* 1995, 36, 1017-1023

[9] S. Sitaula, S. D. Branch, M. F. Ali, *Chemical Communications* 2012, 48, 9284-9286; G. Jie, J. Yuan, J. Zhang, *Biosensors and Bioelectronics* 2012, 31, 69-76; X. He, Z. Li, X. Jia, K. Wang, J. Yin, *Talanta* 2013, 111, 105-110

[10] a N. V. Padhye, M. P. Doyle, *Applied and Environmental Microbiology* 1991, 57, 2693-2698; b R. D. Petty, L. A. Sutherland, E. M. Hunter, I. A. Cree, *Journal of Bioluminescence and Chemiluminescence* 1995, 10, 29-34 solid polymeric structures are in the shape of a pill, tablet or capsule, with separate polymeric structures forming separate layers surrounding each other wherein a layer on the outside of the pill, tablet or capsule comprises reagents that must react first in the chemical reaction and the remaining layers are arranged internally to the outside layer in an order that corresponds to an order required to perform the chemical reaction.

4. The device of claim 1, wherein the two or more reagents are entrapped in the same solid polymeric structure.

The invention claimed is:

1. A device comprising two or more reagents entrapped in the same solid polymeric structure or in separate solid polymeric structures wherein the solid polymeric structure or structures are prepared from an aqueous solution comprising about 10% (w/v) to about 13% (w/v) of pullulan and at least one of the two or more reagents is selected from one or more different reagents that are a protein, antibody, peptide, nucleic acid, phage, antidote and vaccine, or at least one of the two or more reagents is a material from a microorganism, or at least one of the two or more reagents is an inorganic or an organic molecule.

2. The device of claim 1, wherein the two or more reagents are entrapped in separate solid polymeric structures and the solid polymeric structures are stacked in layers on top of each other.

3. The device of claim 1, wherein the two or more reagents are for performing a chemical reaction and are entrapped in separate solid polymeric structures and the 5. The device of claim 1, wherein one or more of the solid polymeric structures are cast onto a substrate comprising at least one of the two or more reagents for a chemical reaction.

6. The device of claim 1, wherein at least one of the two or more reagents is a material from a microorganism.

7. The device of claim 1, wherein at least one of the two or more reagents is an inorganic or an organic molecule.

8. The device of claim 7, wherein the inorganic molecule is selected from one or more different reagents that are an inorganic acid, an inorganic base, an alkaline earth metal carbonate, an alkaline earth metal sulfate, an alkali metal carbonate, an alkali metal sulfate and a metal complex.

9. The device of claim 7, wherein the organic molecule is selected from one or more different molecules that are indoxyl acetate, luciferin, lactate, acetaldehyde, chelating agents, NTPs (ATP, GTP, UTP and CTP) and dNTPs (dATP, dGTP, dTTP and dCTP).

10. The device of claim 1, wherein the two or more reagents are in separate polymeric structures and the two or more reagents that are in separate polymeric structures comprise reagents to perform the Simon's test for secondary amines.

11. The device of claim 10, wherein a top or first layer in a stacked sensor, or a first or outer layer of a pill, tablet or capsule, comprises acetaldehyde and a second or inner layer comprises sodium nitroprusside and sodium carbonate.

12. A method of performing a single step or multi-step chemical reaction comprising:
a) combining two or more reagents for the reaction, either separately or together, with an aqueous pullulan solution to provide reagent pullulan solutions or a reagent pullulan solution, respectively, wherein the aqueous pullulan solution comprises about 10% (w/v) to about 13% (w/v) of pullulan;
b) drying the reagent pullulan solutions or the reagent pullulan solution to provide solid polymeric structures or a solid polymeric structure, respectively; and
c) if the two or more reagents are in separate solid polymeric structures in b), then treating the solid polymeric structures under conditions to dissolve the solid polymeric structures for the two or more reagents to interact in a chemical reaction; or
d) if the two or more reagents are together in the solid polymeric structure in b), then treating the solid polymeric structure under conditions to dissolve the solid polymeric structures for the two or more reagents to interact in a chemical reaction, wherein the solid polymeric structures are or the solid polymeric structure is the component(s) of the device of claim 1.

13. The method of claim 12, wherein, the two or more reagents are in separate solid polymeric structures and the solid polymeric structures are stacked in layers on top of each other.

14. The method of claim 13, wherein the layers are stacked in an order that corresponds to an order required to perform the chemical reaction.

15. The method of claim 12, wherein the two or more reagents are in separate solid polymeric structures and the solid polymeric structures are in the shape of a pill, tablet or capsule, with each separate polymeric structure forming separate layers surrounding each other wherein a layer on the outside of the pill, tablet or capsule comprises reagents that must react first in the chemical reaction and the remaining layers are arranged internally to the outside layer in an order that corresponds to an order required to perform the chemical reaction.

16. The method of claim 15, wherein timing of dissolution of the layers is controlled to allow sufficient reaction time for each step of the chemical reaction.

17. The method of claim 16, wherein the timing is controlled by one or more of thickness of the layers and pullulan concentration.

18. The method of claim 12, wherein the two or more reagents are in the same solid polymeric structure.

19. The method of claim 12, wherein the two or more reagents are in separate solid polymeric structures and the solid polymeric structures are each dissolved in a single water or buffer solution to release the two or more reagents for interaction in the chemical reaction.

* * * * *

UNITED STATES PATENT AND TRADEMARK OFFICE
CERTIFICATE OF CORRECTION

| | |
|---|---|
| PATENT NO. | : 11,067,569 B2 |
| APPLICATION NO. | : 16/274616 |
| DATED | : July 20, 2021 |
| INVENTOR(S) | : Carlos Filipe et al. |

Page 1 of 1

It is certified that error appears in the above-identified patent and that said Letters Patent is hereby corrected as shown below:

In the Claims

Claim 1, Column 39, Line 57, "antidote and vaccine, or at least" should read --antidote or vaccine, or at least--

Claim 8, Column 40, Line 60, "sulfate and a metal complex." should read --sulfate or a metal complex.--

Claim 9, Column 40, Line 64, "NTPs (ATP, GTP, UTP and CTP) and dNTPs" should read --NTPs (ATP, GTP, UTP or CTP) or dNTPs--

Claim 9, Column 40, Line 65, "dGTP, dTTP and dCTP)." should read --dGTP, dTTP or dCTP).--

Signed and Sealed this
First Day of August, 2023

Katherine Kelly Vidal
*Director of the United States Patent and Trademark Office*